(12) United States Patent
Corrie et al.

(10) Patent No.: US 6,765,014 B1
(45) Date of Patent: Jul. 20, 2004

(54) 1-ACYL-7-NITROINDOLINE DERIVATIVES, THEIR PREPARATION AND THEIR USE AS PHOTOCLEAVABLE PRECURSORS

(75) Inventors: John Edgar Thomas Corrie, Knebworth (GB); George Papageorgiou, New Barnet (GB)

(73) Assignee: Medical Research Council, London (GB)

(*) Notice: Subject to any disclaimer, the term of this patent is extended or adjusted under 35 U.S.C. 154(b) by 0 days.

(21) Appl. No.: 09/936,975

(22) PCT Filed: Mar. 20, 2000

(86) PCT No.: PCT/GB00/01039
§ 371 (c)(1),
(2), (4) Date: Dec. 27, 2001

(87) PCT Pub. No.: WO00/55133
PCT Pub. Date: Sep. 21, 2000

(30) Foreign Application Priority Data

Mar. 18, 1999 (GB) .............................................. 9906192

(51) Int. Cl.[7] ..................... C07D 209/04; A61K 31/404
(52) U.S. Cl. ...................................... 514/415; 548/491
(58) Field of Search ........................ 548/491; 514/415; 530/314, 316

(56) References Cited

U.S. PATENT DOCUMENTS

| 4,210,590 A | 7/1980 | Maryanoff et al. |
| 6,268,389 B1 | 7/2001 | Esser et al. |

FOREIGN PATENT DOCUMENTS

| WO | WO 86/00527 | 1/1986 |

OTHER PUBLICATIONS

Goissis, G. et al., "Synthesis of Protected Peptide Acids and Esters by Photosolvolysis of 1–peptidyl–5–bromo–7–nitroindolines"; Proc. Am. Peptide Symp., 5: 559–61 (1977).
Yeda Research and Development Co., Ltd., "Reversible blocking of acyl groups during organic synthesis using 7–nitroindoline derivatives as blocking agents"; Chem. Abstracts, Ab. No. 181004x, 92(21): 637 (1980).
Pass, S. et al., "Racemization–Free Photochemical Coupling of Peptide Segments"; J. Am. Chem. Soc. 103: 7674–7675 (1981).
Adams, S.R. et al., "Biologically Useful Chelators That Take Up $Ca^2$upon illumination"; J. Am. Chem. Soc. 111: 7957–7968 (1989).
Papageorgiou, G. et al., "Photorelease of Carboxylic Acids from 1–Acyl–7–nitroindolines in Aqueous Solution: Rapid and Efficient Photorelease of L–Glutamate"; J. Am. Chem. Soc. 121: 6503–6504 (1999).
Corrie, J.E.T. et al., "Caged Nucleotides and Neurotransmitters"; Bioorganic Phytochemistry, vol. 2: Biological Applications of Photochemical Switches; Morrison, H. (Ed.), Chapter 5: 243–305 (John Wiley & Sons, 1993).

Adams, S.R. et al., "Controlling Cell Chemistry with Caged Compounds"; Annu. Rev. Physiol. 55: 755–784 (1993).
Kaplan, J.H., "Photochemical Manipulation of Divalent Cation Levels"; Annu. Rev. Physiol. 52: 897–914 (1990).
Papageorgiou, G. et al., "Synthetic and Photochemical Studies of N–Arenesulfonyl Amino Acids"; Tetrahedron 55: 237–254 (1999).
Givens, R.S. et al., "New Photoactivated Protecting Groups. 7. p–Hydroxyphenacyl: A Phototrigger for Excitatory Amino Acids and Peptides"; J. Am. Chem. Soc. 119: 8368–8370 (1997).
Furuta, T. et al., "Brominated 7–hydroxycoumarin–4–ylmethyls: Photolabile protecting groups with biologically useful cross–sections for two photon photolysis"; Proc. Natl. Acad. Sci. USA 96: 1193–1200 (1999).
Papageorgiou, G. et al., "Synthesis and Properties of Carbamoyl Derivatives of Photolabile Benzoins"; Tetrahedron 53(11): 3917–3932 (1997).
Amit, B. et al., "Light–Sensitive Amides. The Photosolvolysis of Substituted 1–Acyl–7–nitroindolines"; J. Am. Chem. Soc. 98: 843–844 (1976).

(List continued on next page.)

*Primary Examiner*—Rita Desai
*Assistant Examiner*—Golam M M Shameem
(74) *Attorney, Agent, or Firm*—Dann, Dorfman, Herrell & Skillman, P.C.

(57) ABSTRACT

Photoreleasable compounds comprising a caging moiety linked to an effector moiety represented by structural formula (I) wherein $R_1$ is hydrogen; $C_{1-10}$ alkyl or substituted alkyl; $O(CH_2)_n$—Y; $N(COZ)(CH_2)_mY$; or $N[(CH_2)_mY'][(CH_2)_NY]$; $R_2$ and $R_3$ are independently selected from: hydrogen; $C_{1-10}$ alkyl or substituted alkyl; or $R_2$ and $R_3$ together are cycloalkyl; $R_4$ is hydrogen; $C_{1-10}$ alkyl or substituted alkyl; phenyl or substituted phenyl; $(CH_2)_nY$; or $(CH_2)_mO(CH_2)_nY$; wherein m and n are independently between 1 and 10; Y and Y' are independently selected from hydrogen, $CO_2H$ or salts thereof or $OPO_3^{2-}$, Z is hydrogen or $C_{1-10}$ alkyl or substituted alkyl; and, X is an effector moiety or a group capable of being coupled or converted to an effector moiety, which are capable of releasing the effector moiety on irradiation, typically by flash irradiation with UV light. The photoreleasable compounds can therefor be used to deliver biologically active effector moieties such as neuroactive amino acids or metal chelators to sites where their activity is required.

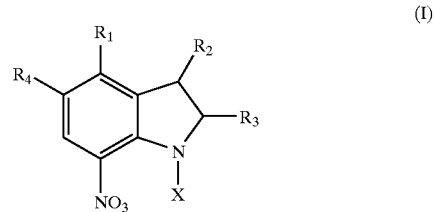

(I)

18 Claims, 7 Drawing Sheets

OTHER PUBLICATIONS

McKillop, A., et al., "Thallium in Organic Synthesis. XXVII. A Simple One–Step Conversion of Acetophenones into Methyl Phenylacetates Using Thallium(III) Nitrate (TTN)"; J. Am. Chem. Soc. 93: 4919–4920 (1971).

Mortensen, M.B. et al., "Improved Preparation of Some Nitroindolines", Org. Prep. Proced. Int. (OPPI Briefs) 28(1): 123–125 (1996).

Carpino, L.A. et al., "Peptide Synthesis via Amino Acid Halides", Acc. Chem. Res. 29(6): 268–274 (1996).

Gall, W.G. et al., "Synthesis of 7–Subsitituted Indoline Derivatives"; J. Org. Chem. 20: 1538–1544 (1955).

Zuman, P. et al., "Addition, Reduction, and Oxidation Reactions of Nitrosobenzene"; Chem. Rev., 94: 1621–1641 (1994).

Barth, A. et al., "Time–Resolved Infrared Spectroscopy of Intermediates and Products from Photolysis of 1–(2–Nitrophenyl)ethyl Phosphates: Reaction of the 2–Nitrosoacetophenone Byproduct with Thiols"; J. Am. Chem. Soc., 119: 4149–4159 (1997).

Wan, P. et al., "Photoredox chemistry of nitrobenzyl alcohols in aqueous solution; Acid and base catalysis of reaction"; Can. J. Chem., 64: 2076–2086 (1986).

Wan, P. et al., "Structure and Mechanism in the Photo–Retro–Aldol Type Reactions of Nitrobenzyl Derivatives. Photochemical Heterolytic Cleavage of C–C Bonds"; J. Am. Chem. Soc., 110(13): 4336–4345 (1988).

Walker, J.W., et al. "Photolabile 1–(2–Nitrophenyl)ethyl Phosphate Esters of Adenine Nucleotide Analogues. Synthesis and Mechanism of Photolysis"; J. Am. Chem. Soc., 110(21): 7170–7177 (1988).

Amit, B. et al., "Light–sensitive Amides. Photocleavage of N–Acyl–1,2,3,4–tetrahydro–8–nitroquinolines to give Free Carboxylic Acids"; J. Chem. Soc., Perkin Tran. I, 57–63 (1976).

Kaplan J.H. et al., "Rapid Photolytic Release of Adenosine 5'–Triphosphate from a Protected Analogue: Utilization by the Na:K Pump of Human Red Blood Cell Ghosts"; Biochemistry, 17(10): 1929–1935 (1978).

Hamill, O.P. et al., "Improved Patch–Clamp Techniques for High–Resolution Current Recording from Cells and Cell–Free Membrane Patches", Pflügers Arch., 391: 85–100 (1981).

Rapp, G. et al., "A low cost high intensity flash device for photolysis experiments"; Pflügers Arch., 411: 200–203 (1988).

Khodakhah, K., et al., "Fast activation and inactivation of inositol trisphosphate–evoked $Ca^2$release in rat cerebellar Purkinje neurones"; J. Physiol., 487.2: 343–358 (1995).

Crabb, T.A. et al., "Microbiological Transformations, Part 6. Microbiological Transformations of Acyl Derivatives of Indoline, 1,2,3,4–Tetrahydroquinoline, 1,2,3,4–Tetrahydroisoquinoline and 2,3,4,5–Tetrahydro–1H–1–benzazepine with the Fungus *Cunninghamella elegans*"; J. Chem. Soc. Perkin Trans. I, 1381–1385 (1985).

Monro, A.M. et al., "The Conformation of the Amide Group in N–Acyl–Indolines and –1,2,3,4–tetrahydroquinolines"; J. Chem. Soc. (B), 1227–1230 (1971).

Terentev, A.P. et al., "Introduction of Substituents in the Benzene Ring of Indole"; J. Gen. Chem. USSR, 29: 2835–2841 (1959).

Corrie, J.E.T. et al., "Synthesis and Absolute Stereochemistry of the Two Diastereoisomers of $p^3$–1–(2–Nitrophenyl)ethyl Adenosine Triphosphate ('Caged' ATP)"; J. Chem. Soc. Perkin Trans. I, 1015–1019 (1992).

Kawase, M. et al., "Silica Gel Assisted Reductive Cyclization of 2–Nitro–a–piperidinostyrenes, Derived from 2–Nitrotoluenes to Indoles"; J. Heterocyclic Chem., 24:1499–1501 (1987).

Buchanan, J.G. et al., "Synthesis of the Indole Nucleoside Antibiotics Neosidomycin and SF–2140"; J. Chem. Soc. Perkin Trans. I, 1417–1426 (1994).

Gangjee, A. et al., "Synthesis and Biological Evaluation of Nonclassical 2,4–Diamino–5–methylpyrido[2,3–d]pyrimidines with Novel Slide Chain Substituents as Potential Inhibitors of Dihydrofolate Reductases"; J. Med. Chem., 40: 479–485 (1997).

Wieland, T. et al., "Synthese einiger Methoxy–oxindole und –indoline"; Chem. Ber., 96: 253–259 (1963) [English translation of Abstract attached].

Kruse, L.I., "Synthesis of 4–Substituted Indoles from o–Nitrotoluenes"; Heterocycles, 16(7): 1119–1124 (1981).

Corrie, J.E.T. et al., "Synthesis and evaluation of photolabile sulfonamides as potential reagents for rapid photorelease of neuroactive amines"; J. Chem. Soc., Perkin Trans. I, 1583–1592 (1996).

Papageorgiou, G. et al., "Effects of Aromatic Substituents on the Photocleavage of 1–Acyl–7–nitroindolines"; Tetrahedron 56: 8197–8205 (2000).

1-ACYL-7-NITROINDOLINE DERIVATIVES, THEIR PREPARATION AND THEIR USE AS PHOTOCLEAVABLE PRECURSORS

FIELD OF THE INVENTION

The present invention relates to photoreleasable compounds, to processes for making and purifying these compounds and to their uses.

BACKGROUND OF THE INVENTION

Photocleavable (caged) reagents that release biologically active compounds rapidly upon flash irradiation with near-UV light are potentially valuable tools for study of biological processes (1). However, reagents that can photorelease effectors such as neuroactive amino acids rapidly and efficiently in aqueous solution have proved elusive. Thus, while there are reports in the prior art of approaches to the problem based on a wide range of different photolabile protecting groups (2), overall these have met with, limited success. Among the better current reagents are the p-hydroxyphenacyl esters described by Givens et al (3), but even these are susceptible to hydrolysis and have poor efficiency of photorelease because of their low extinction coefficient in the 300–350 nm region. A very recent report (4) describes photorelease of L-glutamate from brominated 7-hydroxycoumarin-4-ylmethyl esters and carbamates but these respectively are susceptible to hydrolysis or are rate-limited by decarboxylation of the photochemically-generated N-carboxyglutamate ($k=\sim150$ $s^{-1}$ at pH 7,21° C.) (5).

Pass et al have also reported the use of 5-bromo-7-nitroindolinyl (Bni) as a protecting group during photochemical peptide synthesis to protect carboxylic groups and activate them on irradiation to couple to other nucleophiles (6b).

SUMMARY OF THE INVENTION

Broadly, the present invention relates to photoreleasable compounds comprising a caging moiety linked to an effector moiety, wherein the compounds are capable of releasing the effector moiety on irradiation, typically by flash irradiation with UV light. The photoreleasable compounds can therefore be used to deliver biologically active effector moieties such as neuroactive amino acids or metal chelators to sites where their activity is required. In preferred embodiments of the invention, the caging moiety is based on 7-nitroindoline and substituted derivatives thereof.

Accordingly, in one aspect, the present invention provides a compound represented by the structural formula:

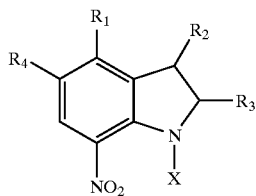

wherein
  $R_1$ is hydrogen;
    $C_{1-10}$ alkyl or substituted alkyl;
    $O(CH_2)_n$—Y;
    $N(COZ)(CH_2)_mY$; or
    $N[(CH_2)_mX][(CH_2)_nY]$;

$R_2$ and $R_3$ are independently selected from:
    hydrogen;
    $C_{1-10}$ alkyl or substituted alkyl; or
    $R_2$ and $R_3$ together are cycloalkyl;
  $R_4$ is hydrogen;
    $C_{1-10}$ alkyl or substituted alkyl;
    phenyl or substituted phenyl;
    $(CH_2)_nY$; or
    $(CH_2)_mO(CH_2)_nY$;
  wherein:
    m and n are independently between 1 and 10;
    X and Y are independently selected from hydrogen, $CO_2H$ or salts thereof or $OPO_3^{2-}$;
    Z is hydrogen or $C_{1-10}$ alkyl or substituted alkyl; and,
    X is an effector moiety or a group capable of being coupled or converted to an effector moeity.

In one embodiment, the present invention provides compounds represented by the structural formula:

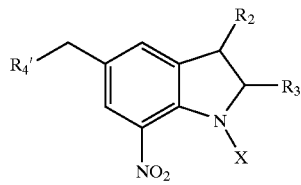

wherein
  $R_2$ and $R_3$ are independently selected from hydrogen $C_{1-10}$ alkyl or substituted alkyl, or $R_2$ and $R_3$ together are cycloalkyl;
  $R_4'$ is a blocking group; and,
  X is an effector moiety.

The $R_4'$ group blocks the 5-position to ensure that the nitration reaction occurs at the 7-position of the indoline ring. Preferably, $R_4'$ is selected from:
  hydrogen;
  $C_1$–$C_{10}$ alkyl or substituted alkyl;
  phenyl or substituted phenyl;
  $(CH_2)_nCO_2Y$; and,
  $(CH_2)_n$—O—$(CH_2)_mY$;
wherein:
  m and n are independently between 0 and 10; and,
  Y is hydrogen, or $C_1$–$C_{10}$ alkyl or substituted alkyl.
Exemplary compounds of the invention include:

Methyl 1-glutaryl-7-nitroindoline-5-acetate 8;
Methyl 1-[(5-dihydroxyphosphoryloxy)pentanoyl)]-7-nitroindoline-5-acetate 9;
Methyl 1-[S-(4-amino-4-carboxybutanoyl)]-7-nitroindoline-5-acetate 10;
Methyl 1-(4-aminobutanoyl)-7-nitroindoline-5-acetate 21;
Methyl 1-acetyl-7-nitroindoline-5-acetate 16;
Mono[1-(5-methoxycarbonylmethyl-7-nitroindolyl)] amide of 1,2-bis(O-aminophenoxy)ethane-N,N,N',N'-tetraacetic acid;
1-Acetyl-4-methoxy-7-nitroindoline 25;
1-Acetyl-4-methoxy-5-methyl-7-nitroindoline 25;
1-[S-(4-Amino-4-carboxybutanoyl)]-4-methoxy-7-nitroindoline;
1-(4-Aminobutanoyl)-4-methoxy-7-nitroindoline;
1-(5-Dihydroxyphosphoryloxy)pentanoyl))-4-methoxy-7-nitroindoline;

Mono[1-(4-methoxy-7-nitroindolyl)] amide of 1,2-bis(O-aminophenoxy)ethane-N,N,N',N'-tetraacetic acid;
1-[S-(4-Amino-4-carboxybutanoyl)]-4-methoxy-5-methyl-7-nitroindoline;
1-(4-Aminobutanoyl)-4-methoxy-5-methyl-7-nitroindoline;
1-[(5-Dihydroxyphosphoryloxy)pentanoyl)]-4-methoxy-5-methyl-7-nitroindoline; and
Mono[1-(4-methoxy-5-methyl-7-nitroindolyl)] amide of 1,2-bis(O-aminophenoxy)ethane-N,N,N',N'-tetraacetic acid.

In some embodiments of the invention, the caging moiety is based on substituted 7-nitroindoline. Examples showing the synthesis of substituted 7-nitroindolinyl glutamate and substituted 7-nitroindolinyl GABA, and the photorelease of L-glutamate and GABA from these compounds is described in the experimental section below.

Preferably, the photoreleasable compound is not an activator or an inhibitor of a biological process mediated by the effector moiety, i.e. the biological activity of the effector is only released when the compound is exposed to electromagnetic radiation (preferably having a wavelength between 300–350 nm), thereby allowing its controlled delivery. Otherwise, it is preferable that (a) the photoreleasable compound is water soluble and stable to hydrolysis and that (b) the release reaction is preferably fast and proceed with high quantum efficiency.

The photoreleasable compounds of the invention have a variety of uses in studying systems that respond to the effector moiety and in the treatment of conditions which respond to it.

In a further aspect, the present invention provides the above compounds for use in a method of medical treatment.

In a further aspect, the present invention provides the use of the above compounds for the preparation of a medicament for the treatment of a condition which responds to the effector moiety.

In a further aspect, the present invention provides a process for releasing an effector moiety, the process comprising irradiating a photoreleasable compound as described above to cause the release of the effector moiety.

In a further aspect, the present invention provides a process for producing one of the above photoreleasable caged compounds, the process comprising:
(a) reacting an indoline to provide a blocking group at the 5-position;
(b) reacting the indoline of step (a) to couple a effector moiety at the heterocyclic nitrogen, the effector group having a protecting group; and,
(c) nitrating the indoline of step (b) at the 7-position.

The sequence of steps specified above has the advantage of avoiding a difficult acylation reaction of 7-nitroindolines. This is advantageous as the conditions required for such a reaction can be detrimental for effector moieties with sensitive side chains such as glutamate.

Conveniently, the protecting group can be selected so that the nitration reaction concurrently removes the protecting group from the effector moiety. This has the advantage that protecting groups present on the effector moiety are concurrently removed in the nitration reaction, In a further aspect, the present invention provides a process for purifying a photoreleasable compound as described above, optionally after producing it as indicated above, the process comprising:
(a) eluting the caged compound from a HPLC column using aqueous methanol containing buffer salts;
(b) desalting fractions containing the caged compound obtained from step (a) on Amberlite XAD-2 resin;
(c) eluting the resin with methanol to recover the caged compound.

The use of this purification procedure to recover the substituted 7-nitroindolinyl GABA is shown in the examples below and is particularly applicable to the purification of photoreleasable compounds having hydrophobic effector groups.

Embodiments of the present invention will now be described by way of example and not by limitation with reference to the accompanying drawings.

DETAILED DESCRIPTION

Effector Moieties

Figure 1:
FIG. 1. Current response of a cultured rat cerebellar granule neurone to photolytic release of L-glutamate from 10. Experimental conditions are given in the text. The arrow marks the commencement of the 1 ms light flash.

The X group can be an effector moiety or a group capable of being coupled or converted to an effector moiety. Examples of effector moieties include labels, drugs, toxins, or carrier or transport molecules. Techniques for coupling the caging moiety to both peptidyl and non-peptidyl coupling partners are well known in the art. In preferred embodiments, the effector moiety is a biologically active compound such as an amino acid (either L or D-amino acids), and more particularly neuroactive amino acids such as L-glutamate, GABA and glycine. The procedures described herein can also be readily adapted to linking larger effector groups such as oligopeptides or polypeptides to the caging moiety. Examples of especially suitable peptides are as follows: thyrotrophin releasing hormone TRH; enkephalins (locally acting endogenous opiates); bradykinin; and angiotensin II. Generally, the methods described herein are applicable to any oligopeptides with non-amidated C-termini.

In further embodiments, the caging compound is attached to an effector moiety which is metal ion chelator thereby providing compounds which on photolysis release the chelator to bind metal ions, e.g. to reduce their concentration in a system. Thus, by way of example, a caging compound can be attached to a carboxylate group containing chelator such as BAPTA (1,2-bis(o-aminophenoxy)ethane-N,N,N',N'-tetraacetic acid), EDTA (ethylenediaminetetraacetate) or EGTA (ethylene glycol bis(β-aminoethyl-ether) N,N,N',N'-tetraacetic acid). These compounds can then be photolysed to chelate $Ca^{2+}$ or other metal ions. An example of a prior art use of compounds capable of releasing metal ion chelators is provided in Adams et al (32), although the effectiveness of the 5,7-dinitroindoline compounds described in this paper is poor.

The synthesis of photoreleasable compounds including oligo or polypeptide effector moieties can be achieved by linking a terminal amino acid (i.e. the C-terminal amino acid) to the caging group and then using polypeptide chain extension techniques to build up the peptide chain stepwise, or by coupling an oligopeptide or polypeptide to the terminal amino acid linked to the caging moiety. Standard peptide synthesis techniques could also be adapted by linking to the synthesis resin the carboxylate group that is present as an ester in the side chain of the compounds shown in the examples. This would give a resin containing the protecting group and C-terminal residue which could be elaborated and eventually cleaved from the resin by standard techniques.

If the photoreleasable compound is synthesized using the scheme described in the examples below, it is preferred that the effector moiety is stable to the nitration reaction carried out after it is attached to the nitrogen of the indole ring. In the case of amino acids, this means that the use of amino acids other than tryptophan, tyrosine, cysteine or methionine is preferred.

In other aspects, the present invention provides precursor compounds in which the effector moiety has not been linked to the caging compound (e.g. X is H or COY as defined above) and/or in which the nitration reaction has not been carried out (e.g. the substituent at the 7-position is hydrogen).

Pharmaceutical Compositions

The photoreleasable compounds described above can be formulated as pharmaceutical compositions. These compositions may comprise, in addition to one or more of the compounds, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, or intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included For intravenous, cutaneous or subcutaneous injection, or injection at the site of affliction, the photoreleasable compound can be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, lactated Ringer's injection. Preservatives, stabilisers, buffers, antioxidants and/or other additives may be included, as required.

After administration, the photoreleasable compound can be activated to release the effector moiety, conveniently by exposure to a flash of UV light. Preferably, the photoreleasable compound according to the present invention is given to an individual in a "prophylactically effective amount" or a "therapeutically effective amount" (as the case may be, although prophylaxis may be considered therapy), this being sufficient to show benefit to the individual. Typically, this will be to cause a therapeutically useful effect in the patient. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration, the data on the efficiency and kinetics of release of the effector moiety and other factors known to practitioners. Examples of the techniques and protocols mentioned above can be found in Remington's Pharmaceutical Sciences, 16th edition, Oslo, A. (ed), 1980.

Materials and Methods

General Procedures. Microanalyses were carried out by MEDAC Ltd., Brunel University, Uxbridge, U.K. Amino acid analyses were performed at the Department of Biochemistry, University of Cambridge, using a Pharmacia AlphaPlus Analyser with ninhydrin detection. $^1$H NMR spectra were determined in $CDCl_3$ with tetramethylsilane as internal standard unless otherwise stated on JEOL FX90Q, Bruker AM 400WB or Varian Unity Plus 500 spectrometers. The $^{13}$C NMR spectrum was determined on a Bruker AM 400WB spectrometer. Positive ion FAB mass spectra at high resolution were obtained on a VG ZAB-SE instrument and negative ion spectra at low resolution were obtained by nanoelectrospray on a Thermoquest LCQ ion trap instrument. IR spectra were in Nujol mulls unless otherwise specified. Merck 9385 silica gel was used for flash chromatography. Organic extracts were dried over $Na_2SO_4$ and solvents were evaporated under reduced pressure. Sodium or ammonium phosphate buffer solutions were prepared from $NaH_2PO_4.2H_2O$ or $NH_4H_2PO_4$ at the specified molarities in water and adjusted to the required pH value with 2 M aq. NaOH. HPLC data were obtained on Waters equipment using a reverse-phase column [Merck Lichrosphere RP8 column (Cat. No. 50832)]. UV detection was with a Waters 484 detector at 254 nm. Preparative HPLC was performed on a 2×30 cm column (Waters $C_{18}$ packing material, Cat. No. 20594). 1-Acetylindoline (20) and 1-acetyl-5-bromoindoline (21) were prepared by literature methods. 5-Bromoindoline (22) was obtained by acidic methanolysis of 1-acetyl-5-bromoindoline (cf preparation of 12). 1,5-Diacetylindoline was prepared as described (23) but using 1,2-dichloroethane instead of carbon disulfide as solvent. 1-(2-Nitrophenylethyl) phosphate (24) was prepared as described (25). 4-Methoxyindole was prepared as described (26), reduced to 4-methoxyindoline as described (27) and acetylated to give 1-acetyl-4-methoxyindoline (28). N,N-Dimethyl-2-methyl-3-nitroaniline was prepared by a modification of a previously described method (29). Amberlite XAD-2 resin (Merck) was purified before use by exhaustive extraction with ethanol in a Soxhlet thimble, until the UV spectrum of the extract showed no absorption.

Results

1-Glutarylindoline 14. A mixture of glutaric anhydride (22.82 g, 200 mmol) and indoline (23.83 g, 200 mmol) in chloroform (240 mL) was stirred at rt for 1 h. The precipitated white solid was filtered and washed with chloroform, and the filtrate was extracted with 5% aqueous $Na_2CO_3$. The aqueous extract was acidified with 4 M HCl and the precipitate was collected. The combined solids were dried and recrystallized (EtOH) to give 14 (29.46 g, 63%), mp 135–136° C.; IR: $v_{max}$/cm$^{-1}$1700, 1660; $^1$H NMR: $\delta_H$ (400 MHz, DMSO-d$_6$) 8.08 (d, J=8 Hz, 1H), 7.22 (d, J=7.3 Hz, 1H), 7.13 (t, J=7.7 Hz, 1H), 6.97 (t, J=7.4 Hz, 1H), 4.04 (t, J=8.5 Hz, 2H), 3.12 (t, J=8.5 Hz, 2H), 2.47 (t, J=7.2 Hz, 2H), 2.31 (t, J=7.2 Hz, 2H) and 1.81 (quintet, J=7.2 Hz, 2H). Anal. Calcd for $C_{13}H_{15}NO_3$: C, 66.94; H, 6.48; N, 6.00. Found: C, 66.96; H, 6.53; N, 5.96.

5-Bromo-1-glutarylindoline 15. Bromine (2.40 g, 15 mmol) was added dropwise to a stirred solution of 1-glutarylindoline 14 (2.33 g, 10 mmol) in glacial acetic acid (30 mL). The mixture was stirred at rt for 1 h, then poured into water (50 mL) and treated with sodium metabisulfite to remove excess bromine. The precipitate was filtered, washed with cold water and dried. Recrystallization ($CH_3CN$) afforded 15 as white crystals (2.79 g, 89%), mp 192–194° C.; IR: $\nu_{max}/cm^{-1}$ 1710, 1655; $^1$H NMR: $\delta_H$ (400 MHz, DMSO-$d_6$) 7.99 (d, J=8 Hz, 1H), 7.39 (m, 1H), 7.30 (dd, J=8.4, 1.4 Hz, 1H), 4.06 (t, J=8.5 Hz, 2H), 3.13 (t, J=8.5 Hz, 2H), 2.46 (t, J=7.2 Hz, 2H), 2.30 (t, J=7.2 Hz, 2H) and 1.80 (quintet, J=7.2 Hz, 2H). Anal. Calcd for $C_{13}H_{14}BrNO_3$: C, 50.02; H, 4.52; N, 4.48. Found: C, 50.31; H, 4.54; N, 4.55.

5-Bromo-1-glutaryl-7-nitroindoline 11. 5-Bromo-1-glutarylindoline 15 (6.25 g, 20 mmol) was added in one portion to a stirred solution of sodium nitrate (1.87 g, 22 mmol) in trifluoroacetic acid (75 mL) and the mixture was stirred at rt for 4 h. The solution was poured into ice-cold water (300 mL) and the precipitated yellow solid was filtered, washed with water and dried in vacuo. Recrystallization [EtOH-MeCN (9:1)] gave 11 as yellow needles (5.50 g, 77%), mp 216–217° C.; UV: $\lambda_{max}$ (EtOH)/nm, 246 ($\epsilon/M^{-1}cm^{-1}$ 17 150), 343 (3000); $\lambda_{max}$ [EtOH-25 mM Na phosphate, pH 7.0 (1:50)]/nm 246 ($\epsilon/M^{-1}cm^{-1}$ 19 200), 346 (2550); IR: $\nu_{max}/cm^{-1}$; 1715, 1685, 1535; $^1$H NMR: $\delta_H$ (400 MHz, DMSO-$d_6$) 7.83 (d, J=1.7 Hz, 1H), 7.81 (d, J=1.7 Hz, 1H), 4.23 (t, J=8.2. Hz, 2H), 3.22 (t, J=8.2 Hz, 2H), 2.54 (t, J=7.2 Hz, 2H), 2.29 (t, J=7.2 Hz, 2H) and 1.77 (quintet, J=7.2 Hz, 2H). Anal. Calcd for $C_{13}H_{14}BrN_2O_5$: C, 43.72; H, 3.67; N, 7.84. Found: C, 43.98; H, 3.65; N, 7.79.

Methyl 1-acetylindoline-5-acetate 2. Thallium nitrate (III) trihydrate (98%) (11.34 g, 25 mmol) was added to a solution of 1,5-diacetylindoline (5.08 g, 25 mmol) in methanol (400 mL) containing perchloric acid (60% w/w) (8 mL) and the mixture was stirred at rt for 4 h. The precipitated solid was filtered off and the filtrate was concentrated to about 50 mL, then diluted with EtOAc and washed with water. The aqueous phase was extracted with EtOAc and the combined organic phases were washed with brine, dried and evaporated to give 2 as light brown crystals (3.94 g, 67%), mp 104–105° C. (EtOAc-hexanes after decolorization with charcoal); IR: $\nu_{max}/cm^{-1}$ 1730, 1645, 1405; $^1$H NMR: $\delta_H$ (90 MHz) 8.12 (d, J=8 Hz, 1H), 6.94–7.16 (m, 2H), 4.02 (t, J=8.3 Hz, 2H), 3.67 (s, 3H), 3.56 (s, 2H), 3.14 (t, J=8.3 Hz, 2H) and 2.18 (s, 3H). Anal. Calcd for $C_{13}H_{15}NO_3$: C, 66.94; H, 6.48; N, 6.00. Found: C, 66.90; H, 6.51; N. 5.96.

Methyl 1-acetyl-7-nitroindoline-5-acetate 16. Compound 2 (467 mg, 2 mmol) was added to a stirred solution of sodium nitrate (170 mg, 2 mmol) in trifluoroacetic acid (5 mL) and the mixture was stirred at rt for 4 h. The solution was poured into ice-cold water (100 mL) and extracted with EtOAc. The combined organic phases were washed with saturated aq. $NaHCO_3$ and brine, dried and evaporated. Recrystallization (EtOAc-hexanes) afforded 16 as orange needles (395 mg, 71%), mp 136–137° C.; IR: $\nu_{max}/cm^{-1}$ 1740, 1670, 1530; $^1$H NMR: $\delta_H$ (90 MHz) 7.52 (br s, 1H), 7.36 (br s, 1H), 4.23 (t, J=8.3 Hz, 2H), 3.70 (s, 3H), 3.62 (s, 2H), 3.20 (t, J=8.3 Hz, 2H) and 2.24 (s, 3H). Anal. Calcd for $C_{13}H_{14}N_2O_5$: C, 62.94; H, 6.27; N, 4.59. Found: C, 63.00; H, 6.16; N, 4.59.

Methyl 1-glutarylindoline-5-acetate 4. A solution of 2 (1.75 g, 7.5 mmol) in a mixture of methanol (100 mL), water (20 mL) and conc. HCl (10 mL) was refluxed for 4 h. The solution was diluted with water (30 mL), concentrated to about 50 mL, basified to pH 8 with $K_2CO_3$ and extracted with EtOAc. The combined organic phases were washed with brine, dried and evaporated to give methyl indoline-5-acetate 3 as a brown oil (1.06 g, 74%); $^1$H NMR: $\delta_H$ (90 MHz) 6.80–7.06 (m, 2H), 6.58 (d, J=8 Hz, 1H), 3.64 (s, 3H), 3.52 (t, J=7.2 Hz, 3H), 3.50 (s, 2H) and 2.96 (t, J=7.2 Hz, 2H). The crude product and glutaric anhydride (685 mg, 6 mmol) were dissolved in chloroform (75 mL) and the mixture was stirred at rt overnight, then refluxed for 2 h. The solution was extracted with saturated aq. $NaHCO_3$ solution and the aqueous extract was acidified to pH 2.8 with conc. HCl and extracted with EtOAc. The latter organic extracts were dried and evaporated to give 4 as white crystals (1.24 g, 74%), mp 134–136° C. (EtOAc-hexanes); IR: $\nu_{max}/cm^{-1}$; 1720, 1.625, 1605; $^1$H NMR: $\delta_H$ (400 MHz) 8.15 (d, J=8 Hz, 1H), 7.07–7.11 (m, 2H), 4.04 (t, J=8.5 Hz, 2H), 3.68 (s, 3H), 3.57 (s, 2H), 3.18 (t, J=8.5 Hz, 2H), 2.52 (t, J=7 Hz, 4H), and 2.06 (quintet, J=7 Hz, 2H). Anal. Calcd for $C_{16}H_{19}NO_5$: C, 56.11; H, 5.07; N,. 10.06. Found: C, 56.18; H, 4.86; N, 10.03.

Methyl 1-glutaryl-7-nitroindoline-5-acetate 8. Compound 4 was added to a stirred solution of sodium nitrate (425 mg, 5 mmol) in trifluoroacetic acid (15 mL) (1.37 g, 4.5 mmol) and the mixture was stirred at rt for 4 h. The solution was poured into ice-cold water (100 mL) and extracted with EtOAc. The combined organic phases were washed with brine, dried and evaporated to give a viscous oil which crystallized after trituration with EtOAc and was recrystallized (EtOAc-hexanes) to give 8 as yellow crystals (1.16 g, 66%), mp 122–124° C.; UV: $\lambda_{max}$ (EtOH)/nm 243 ($\epsilon/M^-$ 1cm$^{-1}$ 17 150), 338 (3010); UV: $\lambda_{max}$ [EtOH-25 mM Na phosphate, pH 7.0 (5:95)]/nm 243.5 ($\epsilon/M^{-1}cm^{-1}$ 16 850), 342 (2770); IR: $\nu_{max}/cm^{-1}$; 1740, 1705, 1680, 1535; $^1$H NMR: $\delta_H$ (400 MHz) 7.55 (s, 1H), 7.38 (s, 1H), 4.24 (t, J=8 Hz, 2H), 3.71 (s, 3H), 3.64 (s, 2H), 3.22 (t, J=8 Hz, 2H), 2.59 (t, J=7 Hz, 2H), 2.51 (t, J=7 Hz, 2H) and 2.05 (quintet, J=7 Hz, 2H). Anal. Calcd for $C_{16}H_{18}N_2O_7$: C, 54.86; H, 5.18; N, 7.99. Found: C, 54.75; H, 5.06 N, 7.97

Methyl 7-nitroindoline-5-acetate 12. A solution of 16 (417 mg, 1.5 mmol) in a mixture of methanol (25 mL), water (5 mL) and conc. HCl (2.5 mL) was heated under reflux for 4 h. The solution was diluted with water (7 mL) and extracted with EtOAc. The combined organic phases were washed with brine, dried and evaporated to give a viscous oil. Trituration with ether and recrystallization ($Et_2O$-hexanes) afforded 12 as red microcrystals (255 mg, 72%), mp 113–115° C.; UV: $\lambda_{max}$ (EtOH)/nm 246 ($\epsilon/M^{-1}cm^{-1}$ 16 600), 431 (5600); $\lambda_{max}$ [EtOH-25 mM Na phosphate, pH 7.0 (1:40)]/nm 238 ($\epsilon/M^{-1}cm^{-1}$ 16 400), 289 (6060), 450 (5060); IR: $\nu_{max}/cm^{-1}$ 3420, 3380, 1740, 1645, 1600, 1520; $^1$H NMR: $\delta_H$ (90 MHz) 7.64 (br s, 1H), 7.16 (br s, 1H), 6.71 (br s, 1H), 3.87 (t, J=8.3 Hz, 2H), 3.69 (s, 3H), 3.51 (s, 2H) and 3.15 (t, J=8.3 Hz, 2H). Anal. Calcd for $C_{11}H_{12}N_2O_4$: C, 55.93; H, 5.12; N, 11.85. Found: C, 55.74; H, 5.07; N, 11.68.

A solution of 4 (70 mg, 0.2 mmol) in $CH_2Cl_2$-dioxane-$H_2O$ (2:3:0.05) (42 mL) was irradiated for 5 h under nitrogen in a Pyrex flask using a 100 W mercury arc lamp. The progress of photolysis was followed by UV spectroscopy. The solution was concentrated in vacuo and the residue was dissolved in EtOAc and washed with saturated aq. $NaHCO_3$ and brine. The organic phase was dried and evaporated and the residue was crystallized (ether-hexanes) to give 12 (44 mg, 95%), mp 113–115° C., identical with material prepared above.

Methyl 7-nitrosoindole-5-acetate 13. A solution of 8 (100 mg, 0.285 mmol) in EtOH (3 mL) was diluted to 60 mL with 50 mM ammonium phosphate, pH 7.0 and irradiated for 5 h under nitrogen in a Pyrex flask, using a 100 W mercury arc lamp. The progress of photolysis was followed by UV spectroscopy. The combined solutions from two such photolyses were diluted with water and extracted with EtOAc. The combined organic phases were washed with saturated aq. NaHCO$_3$ and brine, dried and evaporated. The residue was flash chromatographed [EtOAc-hexanes (1:4)] to give 13 as green needles (24 mg, 19%), mp 110–111° C. (Et$_2$O-hexanes); UV: $\lambda_{max}$ (EtOH)/nm 261 ($\epsilon$/M$^{-1}$cm$^{-1}$ 7740), 400 (7260); $\lambda_{max}$ [EtOH-25 mM Na phosphate, pH 7.0 (1:9)]/nm 278 ($\epsilon$/M$^{-1}$cm$^{-1}$ 6040), 412 (7000); IR: $\nu_{max}$/cm$^{-1}$ (CHCl$_3$) 3460, 1735, 1430, 1395, 1335, 1270, 1180, 1160; $^1$H NMR: $\delta_H$ (500 MHz) 10.20 (br s, 1H), 9.11 (d, J$_{4,6}$=1.3 Hz, 1H, 6-H), 7.97 (d, J$_{4,6}$=1.3 Hz, 1H, 4-H), 7.26 (dd, J$_{2,3}$=3.2 Hz, J$_{1,2}$=3.2 Hz, 1H, 2-H), 6.56 (dd, J$_{2,3}$=3.2 Hz, J$_{1,3}$=2.25 Hz, 1H, 3-H), 4.00 (s, 2H, ArCH$_2$) and 3.76 (s, 3H, OMe); $^{13}$C NMR: $\delta_c$ (100 MHz) 172.0 (C=O), 155.1 (C-7), 136.2 (C-6), 131.9 (C-4), 131.7. (C-3a or C-7a), 127.9 (C-2), 126.2 (C-5), 116.7 (C-7a or C-3a), 103.1 (C-3), 52.3 (OCH$_3$) and 40.6 (CH$_2$). FAB-MS: m/e (M+H)$^+$ Calcd for C$_{11}$H$_{10}$N$_2$O$_3$+H: 219.0770. Found: 219.0762. The $^1$H NMR assignments were made from a combination of the 1-dimensional spectrum and nOe experiments, and a COSY spectrum. $^{13}$C assignments were made using HSQC and HMBC experiments.

Methyl 1-(5-hydroxypentancyl)-7-nitroindoline-5-acetate 5. To a solution of the acid 8 (350 mg, 1 mmol) in dry THF (20 mL) at −10° C. under nitrogen was added dropwise 1 M BH$_3$.THF (2 mL, 2 mmol). The mixture was stirred at −10° C. for 2.5 h, then quenched with water. The aqueous solution was saturated with K$_2$CO$_3$ and extracted with EtOAc. The combined organic phases were washed with brine, dried and evaporated to give a yellow solid. Recrystallization (EtOAc-hexanes) gave 5 as yellow needles (213 mg, 63%), mp 133–135° C.; IR: $\nu_{max}$/cm$^{-1}$; 3500, 1715, 1680, 1535; $^1$H NMR: $\delta_H$ (400 MHz) 7.55 (br s, 1H), 7.37 (br s, 1H), 4.24 (t, J=8 Hz, 2H), 3.70 (s, 3H), 3.66 (t, J=7.8 Hz, 2H), 3.63 (s, 2H), 3.21 (t, J=8 Hz, 2H), 2.53 (t, J=7 Hz, 2H), 1.83 (quintet, J=7 Hz, 2H) and 1.63–1.69 (m, 3H). Anal. Calcd for C$_{16}$H$_{20}$N$_2$O$_6$: C, 57.14; H, 5.99; N, 8.32. Found: C, 57.02; H, 5.90; N. 8.18.

Methyl 1-{5-[di(tort-butoxy)phosphoryloxy]pentanoyl}-7-nitroindoline-5-acetate 6. To a solution of the alcohol 5 (101 mg, 0.3 mmol) in dry THF (6 mL) under nitrogen was added 1H-tetrazole (126 mg, 1.8 mmol) and di-tert-butyl-N,N-diethylphosphoramidite (150 mg, 0.6 mmol, 167 ml) and the mixture was stirred at rt for 3 h. The solution was cooled to 0° C., treated dropwise over 5 min with a solution of m-chloroperbenzoic acid (55% peracid; 288 mg, 1 mmol) in CH$_2$Cl$_2$ (2 mL)-and stirred at 4° C. for 1 h, then diluted with ether (20 mL) ; washed with 10% aq. Na$_2$S$_2$O$_5$. The organic phase was separated and the aqueous phase was re-extracted with ether. The combined organic phases were washed successively with 10% aq. Na$_2$S$_2$O$_5$, saturated aq. NaHCO$_3$, 0.5 M aq. NaOH and brine, dried and evaporated. Flash chromatography (EtOAc) followed by trituration with ether afforded 6 as yellow needles (111 mg, 70%), mp 105–106° C. (EtOAc-hexanes); IR: $\nu_{max}$/cm$^{-1}$; 1745, 1680, 1535, 1000, 985; $^1$H NMR: $\delta_H$ (400 MHz) 7.54 (d, J=0.8 Hz, 1H), 7.36 (d, J=0.8 Hz, 1H), 4.23 (t, J=8 Hz, 2H), 3.98 (dt, J$_{H,P}$=6.3 Hz, J=7 Hz, 2H), 3.70 (s, 3H), 3.62 (s, 2H), 3.20 (t, J=8 Hz, 2H) 2.52 (t, J=7 Hz, 2H), 1.73–1.88 (m, 4H) and 1.47 (s, 18H). Anal. Calcd for C$_{24}$H$_{37}$N$_2$O$_9$P.½H$_2$O: C, 53.63; H, 7.13; N, 5.21. Found: C, 53.52; H, 6.99; N, 5.21.

Methyl 1-[5-dihydroxyphosphoryloxy)pentanoyl]-7-nitroindoline-5-acetate 9 and 1-[5-di-hydroxyphosphoryloxy)pentanoyl]-7-nitroindoline-5-acetic acid 17. A solution of the phosphate ester 6 (141 mg, 0.266 mmol) in TFA (3 mL) was stirred at rt for 4 h and evaporated under reduced pressure. The residue was dissolved in water and the pH was adjusted to 6.5. The aqueous solution was washed with ether, analyzed by reverse-phase HPLC (mobile phase 25 mM Na phosphate, pH 6.0+50% MeOH at 1.5 mL/min) and quantified by UV absorption at 342 nm (234 $\mu$mol, 88%). HPLC showed a major peak with t$_R$ 5.6 min and a minor peak at 1.8 min. The solution was lyophilized and the two components were separated by preparative HPLC (25 mM Na phosphate, pH 6.0, 2.5 mL/min). The column was first fluted with buffer for 1 h, then with water for 1 h. The peak eluted with water was collected and the column was then eluted with water-MeOH (100:15 v/v). Fractions corresponding to the first peak were combined and quantified by UV spectroscopy to give the acid 17 (Na$^+$ salt) (8.5 $\mu$mol, 3%); $^1$H NMR: $\delta_H$ (400 MHz, D$_2$O, acetone ref.) 7.57 (d, J=0.8 Hz, 1H), 7.51 (d, J=0.8 Hz, 1H), 4.35 (t, J=8 Hz, 2H), 3.84 (dt, J$_{H,P}$=6.2 Hz, J=7 Hz, 2H), 3.58 (s, 2H), 3.25 (t, J=8 Hz, 2H), 2.67 (t, J=6.9 Hz, 2H) and 1.68–1.77 (m, 4H). The fractions containing the peak eluted by water-MeOH were combined and quantified by UV spectroscopy to give 9 (Na$^+$ salt) (141 $\mu$mol, 53%); $^1$H NMR: $\delta_H$ (400 MHz, D$_2$O, acetone ref.) 7.66 (s, 1H), 7.57 (s, 1H), 4.39 (t, J=8 Hz, 2H), 3.86 (dt, J$_{H,P}$=6.2 Hz, J=7 Hz, 2H), 3.85 (s, 2H), 3.76 (s, 3H), 3.28 (t, J=8 Hz, 2H), 2.70 (t, J=6.9 Hz, 2H) and 1.70–1.77 (m, 4H). ES-MS, m/e (M+H)$^-$ Calcd for C$_{16}$H$_{19}$N$_2$O$_9$P+H: 415. Found: 415.

Methyl 1-(S-[4-tert-butoxycarbonyl)-4-(tert -butoxycarbonylamino)]butanoyl)indoline-5-acetate 7. Crude 3 (327 mg, 1.9 mmol) was prepared as described above (see compound 4), dissolved in dry MeCN (30 mL) and treated with DMAP (611 mg, 5 mmol) and N-tert-BOC-L-glutamic acid $\alpha$-tert-butyl ester (607 mg, 2 mmol), followed by 1-(3-dimethylaminopropyl)-3-ethylcarbodiimide (422 mg, 2.2 mmol). The mixture was stirred at rt for 18 h, then evaporated and the residue was dissolved in EtOAc and washed successively with 0.5 M aq. HCl, saturated aq. NaHCO$_3$ and brine, dried and evaporated to give a viscous oil. Flash chromatography [EtOAc-hexanes (55:45)] and trituration with ether gave. 6 as white crystals (626 mg, 69%), mp 80–81° C. (EtOAc-hexanes); IR: $\nu_{max}$/cm$^{-1}$; 3340, 1730, 1680, 1655, 1625; $^1$H NMR: $\delta_H$ (400 MHz) 8.15 (d, J=8 Hz, 1H), 7.07–7.11 (m, 2H), 5.23 (d, J=6.9 Hz, 1H), 4.22 (m, 1H), 4.03 (2×t, J=8.5 Hz, 2H; rotamers), 3.68 (s, 3H), 3.57 (s, 2H), 3.17 (t, J=8.5 Hz, 2H), 2.43–2.59 (m, 2H), 2.18–2.31 (m, 1H), 1.98–2.07 (m, 1H), 1.47 (s, 9H) and 1.41 (s, 9H). Anal. Calcd for C$_{25}$H$_{36}$N$_2$O$_7$: C, 63.01; H, 7.61; N, 5.88. Found: C, 63.08; H, 7.81; N, 5.64.

Methyl 1-[S-(4-amino-4-carboxybutanoyl)]-7-nitroindoline-5-acetate 10 and 1-[S-(4-amino-4-carboxybutanoyl)]-7-nitroindoline-5-acetic acid 18. To a stirred solution of sodium nitrate (93 mg, 1.1 mmol) in trifluoroacetic acid (5 mL) was added the tert-BOC glutamate derivative 6 (477 mg, 1 mmol) and the mixture was stirred at rt for 4 h. The solution was concentrated in vacuo and residue was dissolved in water (30 mL) and adjusted to pH 6.2 with 1 M aq. NaOH. The solution was washed with ether and analyzed by reverse-phase HPLC (mobile phase 25 mM Na phosphate, pH 6.0+50% MeOH at 1.5 mL/min) and quantified by UV absorption at 342 nm (819 $\mu$mol, 74%). HPLC showed a major peak with t$_R$ 5.2 min and a minor peak at 1.9 min. The solution was lyophilized and the components were separated by preparative HPLC (mobile phase 25 mM Na phosphate, pH 6.0, 2.5 mL/min). The column was first eluted with buffer for 1 h, then with water for 1 h. Fractions eluted with water were collected and the column was then eluted with water-MeOH (2:1 v/v). Fractions containing the peak that eluted with water were combined, analyzed and quantified (UV spectroscopy) to give the acid 18 (Na$^+$ salt) (18.4 μmol, 3%); $^1$H NMR: δ$_H$ (400 MHz, D$_2$O, acetone ref.) 7.58 (s, 1H), 7.51 (s, 1H), 4.32 (t, J=8 Hz, 2H), 3.79 (t, J=6.2 Hz, 1H), 3.58 (s, 2H), 3.25 (t, J=8 Hz, 2H), 2.80 (t,=7.5 Hz, 2H) and 2.19 (q, J=7.2 Hz, 2H). The fractions containing the second peak were combined and quantified (UV spectroscopy) to give 10 (Na$^+$ salt) (478 μmol, 81%); $^1$H NMR: δ$_H$ (400 MHz, D$_2$O, acetone ref.) 7.62 (d, J=0.7 Hz, 1H), 7.54 (d, J=0.7 Hz, 1H)., 4.32 (t, J=8 Hz, 2H), 3.81 (s, 2H), 3.78 (t, J=6.3 Hz, 1H), 3.72 (s, 3H), 3(t, J=8 Hz, 2H), 2.79 (t, J=7.5 Hz, 2H) and 2.19 (q, J=7.2 Hz, 2H). FAB-MS: m/e (M+H)$^+$ Calcd for C$_{16}$H$_{19}$N$_3$O$_7$+H: 366.1301. Found: 366.1279.

Hydrolytic stability of 1-acyl-7-nitroindolines. Solutions of compounds 17 and 18 (each ~0.2 mM) were prepared in.62.5 mM Na phosphate, pH 12.01 and incubated at 30° C. Aliquots (125 μL) of each solution were withdrawn at 0, 1, 2, 4, 8, 24, 32, and 48 h, quenched with 200 mM Na phosphate, pH 6.0 (125 μL) and stored frozen prior to analysis. The extent of hydrolysis was determined by reverse-phase HPLC analysis (mobile phase 25 mM Na phosphate, pH 6.0+10% MeOH, 1.5 ml/min). Retention times were 7.4 and 4.4 min for 17 and 18 respectively. Quantification was based on peak heights compared to those of unhydrolysed controls (t$_o$). First-order rate constants for hydrolysis were obtained from single exponential fits to the data. Half-times for hydrolysis were 29 h and 6 h for compounds 17 and 18 respectively.

Figure 2:
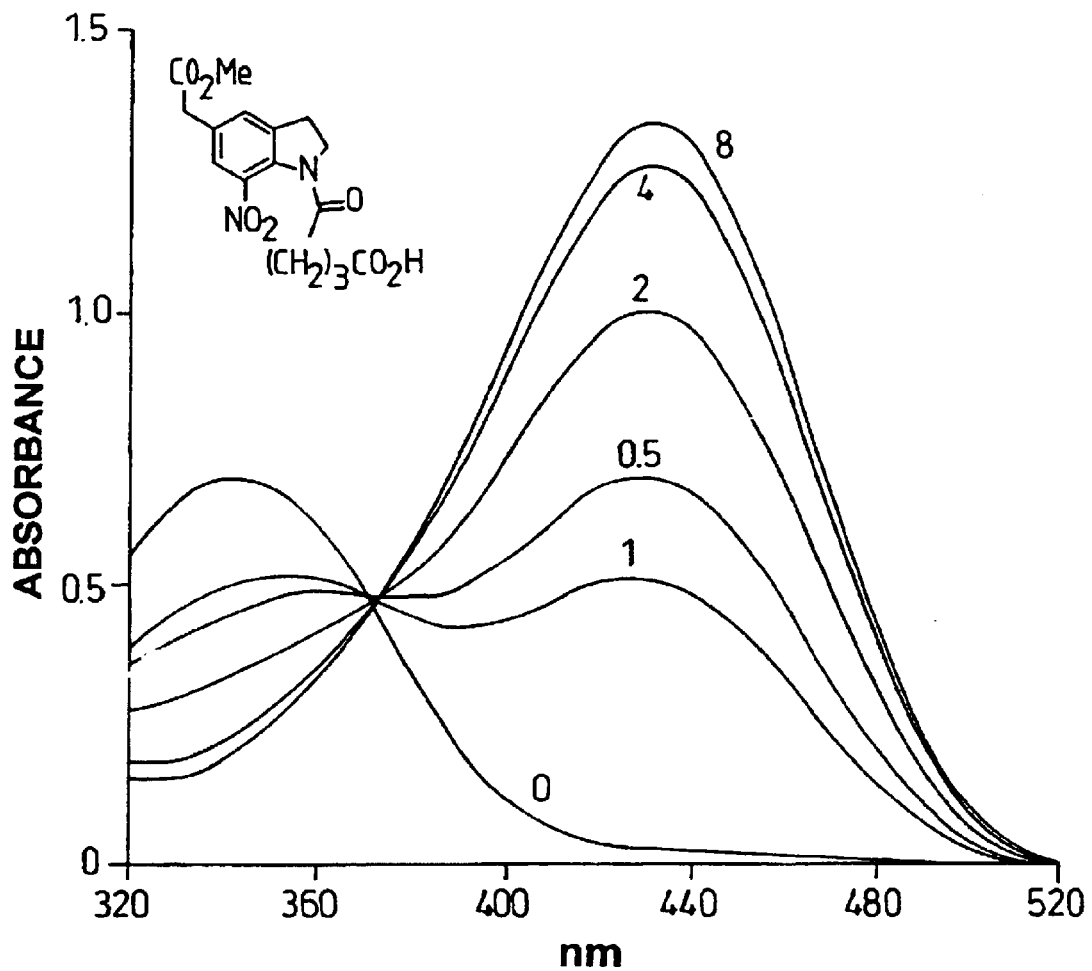
FIG. 2: Photolysis of 8 in $CH_2Cl_2$-dioxane-$H_2O$ (2:3:0.05). Numbers on the traces indicate the cumulative time of irradiation (in minutes).
Figure 3:
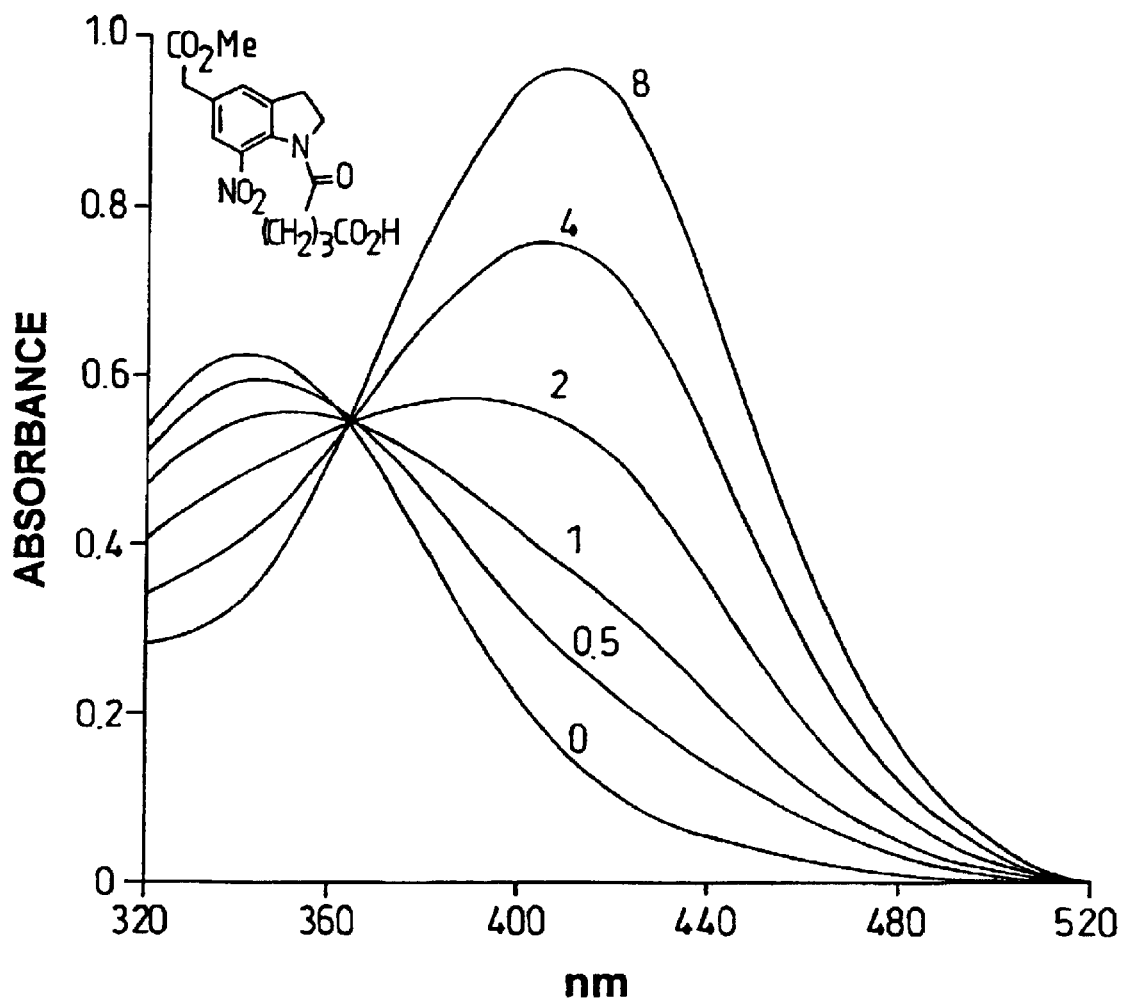
FIG. 3: Photolysis of 8 in pH 7 aqueous buffer. Numbers on the traces indicate the cumulative time of irradiation (in minutes).

Analytical photolysis of 8 in organic and aqueous solvents. Solutions (~0.25 mm) of 8 in either CH$_2$Cl$_2$-dioxane-H$_2$O (2:3:0.05) or 25 mM Na phosphate, pH 7.0 were irradiated in air for times between 0 and 16 min in a 1-cm path length cell with light from a 100 W xenon arc lamp, filtered through a Hoya 340 filter. UV-Vis spectra were recorded at intervals and the overlaid spectra are shown in FIGS. 2 and 3 respectively.

Relative photolysis efficiencies of 8 and 11. A solution containing both 8 and 11 (each 0.5 mM) in 25 mM Na phosphate, pH 7.0 was irradiated in a 1-mm path length cell using light from a 100 W xenon arc lamp which passed through Hoya 340 and Schott WG 305 filters before. illuminating the cell. The extent of photolysis of each compound was determined by reverse-phase HPLC analysis (mobile phase 10 mM Na phosphate, pH 6.0+50% MeOH, 1.5 mL/min). Retention times for 8 and 11 were 3.8 and 7.8 min respectively. After 2 min irradiation, the extents of conversion for compounds 8 and 11 were 40 and 16% respectively.

Quantum yield estimation for 10. A solution of 1-(2-nitrophenylethyl) phosphate and 10 (each 0.50 mM) together with dithiothreitol (5 mM) was prepared in 25 mM ammonium phosphate, pH 7.0. Aliquots of the solution (5×25 ml) in a 1-mm path length cell were each subjected to one 50-ns flash from a frequency-doubled ruby laser, that delivered 347 nm light with an average energy of 90 mJ (range 83–104 mJ). The combined irradiated solutions were analyzed by reverse-phase HPLC (mobile phase 25 mM Na phosphate, pH 6.0+40% MeOH, 1.5 ml/min). Retention times were 4.2 and 7.2 min for 10 and 1-(2-nitrophenylethyl) phosphate respectively. Quantification was based on peak heights compared to those of the unphotolyzed control. Extinction coefficients at 347 nm used to calculate the relative quantum yields were 2720 and 510 M$^{-1}$cm$^{-1}$ for 10 and 1-(2-nitrophenylethyl) phosphate respectively. Photolysis and product analysis for compounds 10 and 18.

Separate solutions of 10 (each 0.50 mM) in 25 mM ammonium phosphate, pH 7.0±1 mM dithiothreitol were irradiated in a 1-mm path length cell for 3 min using light from a mercury arc lamp which passed through Hoya 340 and Schott WG 305 filters before illuminating the cell. The extent of photolysis was determined by reverse-phase HPLC (mobile phase 25 mM Na phosphate, pH 6.0+10% MeOH, 1.5 ml/min). Quantification was based on peak heights compared to those of unphotolyzed controls. Aliquots of the photolyzed solutions were also subjected to quantitative amino acid analysis (see General Procedures). Each sample was photolyzed to ~35% conversion and measured concentrations of glutamate were 90–94% of the values calculated from the extent of photolysis. Maximum contamination of the unphotolyzed samples by free glutamate was 0.25%.

Corresponding experiments with compound 18 at ~51% photolysis gave measured concentrations of glutamate of 97–108% of the values calculated from the extent of photolysis. Free glutamate was not detectable in the unphotolyzed solution of 18.

Synthesis of caged GABA. Synthesis of the caged GABA 21 was essentially as described for the glutamate compound 10 (see main text and Supporting Information), starting from the protected derivative 19 (see Experimental Details below). The principal difference was in the isolation protocol, where the properties of the caged GABA required a change of method. Purification of the caged glutamate 10 was effected by preparative HPLC, in which initial elution of the column with aqueous buffer, followed by pure water, sufficed to remove inorganic salts and also separated the small amount of compound 18 that had the hydrolyzed side chain. Elution with water-MeOH (2:1) then gave the pure glutamate compound10. In the case of the GABA reagent, which had only one charged group, the compound was significantly more hydrophobic and could not be eluted from a preparative HPLC column using a similar protocol. Instead the compound was eluted from the preparative HPLC column using a mobile phase of aqueous methanolic buffer (see below). Early fractions were contaminated with material assumed to be the hydrolyzed compound 20 but subsequent fractions contained only the required compound 21. This material was desalted by absorption on Amberlite XAD-2 resin, that was washed with water to remove buffer salts, then eluted with methanol to recover the caged GABA 21. As for the caged glutamate 10, photolysis and quantitative amino acid analysis showed stoichiometric release of GABA.

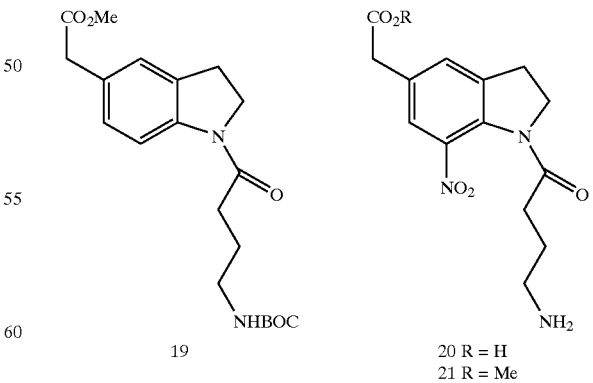

Methyl 1-[4-(tert-butoxycarbonyla mino)]butanoyl] indoline-5-acetate 19. A solution of the crude indoline 3 (291 mg, 1.52 mmol) and 1-hydroxybenzotriazole (540 mg, 4 mmol) under nitrogen in dry THF (15 mL) was cooled to 0°

C. and treated with N-BOC-γ-aminobutyric acid (406 mg, 2 mmol), followed by dropwise addition of DCCI (433 mg, 2.1 mmol) in dry THF (5 mL). The mixture w stirred at 0° C. for 1 h, then at rt overnight. The precipitate was filtered and washed with THF, and the combined filtrates were evaporated. A solution of the residue in EtOAc was washed with dilute aq. HCl aq. NaHCO$_3$ and brine, dried and evaporated. Flash chromatography [EtOAc-hexanes (1:1)] gave 19 (309 mg, 54%), mp 85–86° C. (EtOAc-hexanes); IR: $v_{max}$/cm$^{-1}$ 3275, 1750, 1710, 1675; $^1$H NMR (400 MHz): δ8.15 (d, J=8 Hz, 1H), 7.10 (s, 1H), 7.08 (d, J=8 Hz, 1H), 4.78 (br s, 1H), 4.04 (t, J=8.5 Hz, 2H), 3.68 (s, 3H), 3.57 (s, 2H), 3.23 (q, J=6.2 Hz, 2H), 3.18 (t, J=8.5 Hz, 2H), 2.46 (t, J=7 Hz, 2H), 1.93 (quintet, J=6.7 Hz, 2H) and 1.42 (s, 9H). Anal. Calcd for $C_{20}H_{28}N_2O_5$: C, 63.81; H, 7.50; N, 7.44. Found: C, 63.67; H, 7.63; N, 7.54.

Methyl 1-(4-aminobutanoyl)-7-nitroindoline-5-acetate 21. Sodium nitrate (93 mg, 1.1 mmol) was added to a stirred solution of 19 (376 mg, 1 mmol) in TFA (5 mL) and the mixture was stirred for 4 h at rt, then evaporated under reduced pressure. The residue was dissolved in water (30 mL) and adjusted to pH 7 with 1 M NaOH. The solution was washed with water, analyzed by reverse-phase HPLC (mobile phase 25 mM Na phosphate, pH 6.0+75% MeOH at 1.5 mL/min) and quantified by UV absorption at 342 nm (819 μmol, 82%). HPLC showed major and minor peaks, $t_R$ 6.6 and 1.9 min respectively. The minor peak was assumed to be the free acid 20. Part of the solution (containing 669 μmol) was lyophilized and purified by preparative HPLC (25 mM Na phosphate, pH 6.0, 2.5,.mL/min). The column was first eluted with buffer for 1 h, then with water for 1 h and finally with 10 mM Na phosphate, pH 6.0+50% MeOH. Fractions eluted by the last of these eluents were analyzed by reverse-phase HPLC as above. Two early fractions contained both the faster and slower eluting components (total 294 μmol) and were discarded. Subsequent fractions contained only the later-eluting ($t_R$ 6.6 min) component and were combined, quantified by UV absorption (383 μmol) and concentrated under reduced pressure to remove most of the methanol. The residue was diluted to ~20 mL and mixed for 20 min with Amberlite XAD-2 beads (5 g). The beads were washed with water to remove inorganic salts, then extracted with MeOH (8×20 mL). The methanolic solution was quantified by UV (269 μmol), evaporated and the residue containing 21 (phosphate salt) was redissolved in water and stored at −20° C.; $^1$H NMR: δ$_H$ (400 MHz, D$_2$O, acetone ref.) 7.61 (d, J=0.7 Hz, 1H), 7.55 (d, J=0.7 Hz, 1H), 4.32 (t, J=8 Hz, 2H), 3.83 (s, 2H), 3.72 (s, 3H), 3.25 (t, J 8 Hz, 2H), 3.08 (t, J=7.8 Hz, 2H), 2.75 (t, J=7 Hz, 2H) and 2.02 (quintet, J=7.5 Hz, 2H). FAB-MS: m/e (M+H)$^+$ Calcd for $C_{15}H_{19}N_3O5$+H: 322.1403. Found: 322.1413.

Photolysis and product analysis for compound 21. A solution (0.5 mM) of 21 in 25 mM ammonium phosphate, pH 7.0 was irradiated as described for compound 10 and the photolyzed solution was quantified by reverse-phase HPLC and amino acid analysis. At 38% photolysis, the measured recovery of GABA was 88% of the value calculated from the extent of photolysis.

1,7-Diacetyl-4-methoxyindoline 22. To a solution of 1-acetyl-4-methoxyindoline (4.02 g, 21 mmol) in dry 1,2-dichloroethane (30 ml) cooled in ice was added acetyl chloride (2.1 ml, 30 mmol). Powdered anhydrous AlCl$_3$ (8.4 g, 63 mmol) was added portionwise with stirring. The mixture was stirred at rt overnight, then warmed to 50° C. for 2 h. The red/brown slurry was poured into acidified cold water (200 ml) and extracted with CH$_2$Cl$_2$. The combined organic phases were washed with 0.5 M aq. NaOH and brine, dried and evaporated to give a brown oil. Flash chromatography (EtOAc) followed by trituration with Et$_2$O afforded 22 as pale yellow needles (2.22 g, 54%), mp 88–89° C., (Found: C, 66.89; H, 6.50; N, 5.95. $C_{13}H_{15}NO_3$ requires C, 66.94; H, 6.48; N, 6.00%); δ$_H$ (90 MHz) 7.33 (1 H, d, J 8.3, H-5), 6.61 (1 H, d, H-6), 4.17 (2 H, t, J 8.1, H-2), 3.85 (3 H, s, OMe), 3.05 (2 H, t, 3-H), 2.44 (3 H, s, 7-Ac) and 2.21 (3 H, s, N-Ac).

Methyl 1-acetyl-4-methoxyindoline-7-acetate 23. Thallium(III) nitrate trihydrate (3.21 g, 7.1 mmol) was added to a solution of 1,7-diacetyl-4-methoxyindoline 22 (1.65 g, 7.1 mmol) in MeOH (70 ml) containing perchloric acid (60% w/w, 1.5 ml) and the mixture was stirred at rt for 4 h. The precipitated white solid was filtered off and the filtrate was concentrated to about 10 ml, diluted with EtOAc (50 ml) and washed with water. The aqueous phase was extracted with EtOAc and the combined organic phases were washed with saturated aq. NaHCO$_3$ and brine, dried and evaporated to give a viscous oil. Flash chromatography [EtOAc-hexanes (4:1)] afforded 23 as white crystals (0.88 g, 47%), mp 80–81° C. (from EtOAc-hexanes) (Found: C, 63.60; H, 6.50; N, 5.28. $C_{14}H_{17}NO_4$ requires C, 63.87; H, 5.51; N, 5.32%); δ$_H$ (90 MHz) 7.04 (1 H, d, J 8.3, H-5), 6.63 (1 H, d, H-6), 4.06 (2 H, t, J 8.1, H-2), 3.81 (3 H, s, OMe), 3.76 (2 H, s, ArCH$_2$), 3.71 (3 H, s, CO$_2$Me), 2.96 (2 H, t, 3-H) and 2.24 (3 H, s, N-Ac).

Methyl 1-acetyl-4-methoxy-5-nitroindoline-7-acetate 24. To a stirred solution of NaNO$_3$ (75 mg, 0.9 mmol) in TFA (4 ml) was added 23 (211 mg, 0.8 mmol). The mixture was stirred at rt for 4 h and the red/brown solution was poured into ice-cold water and extracted with EtOAc. The organic extracts were washed with saturated aq. NaHCO$_3$ and brine, dried and evaporated to give a brown solid. Flash chromatography (EtOAc) and recrystallisation from EtOAc-hexanes afforded 24 as pale yellow needles (90 mg, 38%), mp 181–182° C. (Found: C, 54.59; H, 5.24; N, 9.03. $C_{14}H_{16}N_2O_6$ requires C, 54.54; H, 5.23; N, 9.08%); $\lambda_{max}$ (EtOH)/nm 314 (ε/M$^{-1}$cm$^{-1}$ 7250); $\lambda_{max}$ [EtOH-25 mM Na phosphate, pH7.0 (5:95)]/nm 325 (ε/M$^{-1}$cm$^{-1}$ 7370); δ$_H$ (90 MHz) 7.74 (1 H, s, H-6), 4.16 (2 H, t, J 8.1, H-2), 3.90 (3 H, s, OMe), 3.78 (2 H, s, ArCH$_2$), 3.69 (3 H, s, CO$_2$Me), 3.15 (2 H, t, 3-H) and 2.27 (3 H, s, N-Ac).

1-Acetyl-4-methoxy-7-nitroindoline 25 and 1-Acetyl-4-methoxy-5-nitroindoline 26. To a stirred solution of NaNO$_3$ (125 mg, 1.5 mmol) in TFA (4 ml) was added 1-acetyl-4-methoxyindoline (287 mg, 1.5 mmol) and the mixture was stirred at rt for 4 h. The red/brown solution was poured into ice-cold water and extracted with EtOAc. The combined organic phases were washed with saturated aq. NaHCO$_3$ and brine, dried and evaporated to give a dark brown viscous oil. Flash chromatography [EtOAc-hexanes (1:1)] afforded two products. The first product eluted was 1-acetyl-4-methoxy-7-nitroindoline 25 as yellow crystals (83 mg, 23%), mp 180–182° C. (from EtOAc-hexanes) (Found: C, 56.05; H, 5.12; N, 11.80. $C_{11}H_{12}N_2O_4$ requires C, 55.93; H, 5.12; N, 11.85%); $\lambda_{max}$ (EtOH)/nm 248 (ε/M$^{-1}$cm$^{-1}$ 17690), 295 (4980); $\lambda_{max}$ [EtOH-25 mM Na phosphate, pH 7.0 (2.5:97.5)]/nm 246 (ε/M$^{-1}$cm$^{-1}$ 15930), [EtOH-25 mM Na phosphate, pH 7.0 (5:95)] 328 (4520); $v_{max}$ (Nujol)/cm$^{-1}$ 1670, 1605, 1520, 1340, 1275; δ$_H$ (600 MHz) 7.75 (1 H, d, J 9.0, H-6), 6.63 (1 H, d, H-5), 4.23 (2 H, t, J 8.1, H-2), 3.91 (3 H, s, 4-OMe), 3.08 (2 H, t, 3-H) and 2.24 (3 H, s, N-Ac). The assignments were made from a combination of the 1-dimensional spectrum and experiments.

The second eluted product was 1-acetyl-4-methoxy-5-nitroindoline 26 as yellow crystals (79 mg, 22%), mp 101–102° C. (from EtOAc-hexanes) $\lambda_{max}$ (EtOH)/nm 238

(ε/M⁻¹cm⁻¹ 9110), 327 (8580); λ$_{max}$ [EtOH-25 mM Na phosphate, pH 7.0 (5:95)]/nm 238 (ε/M⁻¹cm⁻¹ 8550), 341 (9240); ν$_{max}$ (Nujol)/cm⁻¹ 1665, 1600, 1520, 1385, 1335; δ$_H$ (500 MHz) 8.01 (1 H, d, J 8.5, H-7), 7.86 (1 H, d, H-6), 4.18 (2 H. t, J 8.5, H-2), 3.93 (3 H, s, 4-OMe), 3.28 (2 H, t, 3-H) and 2.26 (3 H, s, N-Ac).

4-Methoxy-5-methylindole 27. To a stirred solution of 2,6-dimethyl-3-nitroanisole (3.26 g, 18 mmol) in dry DMF (36 ml) were added DMF dimethyl acetal (2.51 g, 19.8 mmol, 2.8 ml) and pyrrolidine (1.8 ml). The reaction mixture was stirred under N$_2$ at 125° C. for 3 h, cooled to rt and concentrated in vacuo. The oily residue was dissolved in a mixture of toluene-acetic acid (5:3, 36 ml) and added to a stirred mixture of iron powder (18 g) and silica gel (70–230 mesh, 45 g) in a mixture of toluene-acetic acid (5:3, 234 ml). The mixture was then heated at reflux under N$_2$ for 1 h, cooled to rt, diluted with CH$_2$Cl$_2$ and filtered. The filter cake was washed thoroughly with CH$_2$Cl$_2$ and the combined filtrates were washed successively with Na$_2$S$_2$O$_5$ solution, saturated aq. NaHCO$_3$ and brine, dried and evaporated. The residue was flash chromatographed [(CH$_2$Cl$_2$-hexanes (3:2)] to give 27 as a colourless viscous oil (0.48 g, 16%) which was used without further purification; δ$_H$ (90 MHz) 8.10 (1 H, br s, NH), 6.88–7.08 (3 H, m, 2-, 6-, and 7-H), 6.50–6.64 (1 H, m, 3-H), 3.98 (3 H, s, OMe) and 2.32 (3 H, s, Me).

4-Methoxy-5-methylindoline 28. To a solution of 4-methoxy-5-methylindole 27 (0.48 g, 2.98 mmol) in acetic acid (20 ml) was added NaBH$_3$CN (0.75 g, 9 mmol) portionwise over 10 min (exothermic reaction) and the mixture was then stirred at rt for 0.5 h. Water (2–3 ml) was added and the solvent removed in vacuo. The residue was dissolved in EtOAc and washed with saturated aq. NaHCO$_3$ and brine, dried and evaporated to give 28 as a viscous oil (449 mg, 92%) which was immediately used in the next step; δ$_H$ (90 MHZ) 6.80 (1 H, d, J 9, 7-H), 6.31 (1 H, d, 6-H), 3.76 (3 H, s, OMe), 3.56 (2 H, t, J 8, 2-H), 3.12 (3 H, t, 3-H) and 2.14 (3 H, s, Me).

1-Acetyl -4ethozy-5methylindoline 29. Crude 4-methoxy-5-methylindoline 28 (449 mg, 2.75 mmol) was dissolved in a mixture of acetic anhydride (10 ml) and glacial acetic acid (10 ml) and the mixture was heated under reflux for 3 h. The solution was cooled to rt and concentrated. The residue was dissolved in EtOAc and washed with water, saturated aq. NaHCO$_3$ and brine, dried and evaporated to 29 as white crystals (388 mg, 69%), mp 139–140° C. (from EtOAc-hexanes) (Found: C, 70.17; H, 7.37; N, 6.85. C$_{12}$H$_{15}$NO$_2$ requires C, 70.22; H, 7.37; N, 6.82%); δ$_H$ (90 MHz) 7.84 (1 H, d, J 8.3, 7-H), 6.99 (1 H, d, 6-H), 4.05 (2 H, t, J 8.3, 2-H), 3.77 (3 H, s, OMe), 3.19 (3 H, t, 3-H), 2.23 (3 H, s, Me) and 2.19 (3 H, s, NAc).

1-Acetyl-4-methoxy-5-methyl-7-nitroindoline 30. To a stirred solution of NaNO$_3$ (140 mg, 1.65 mmol) in TFA (5 ml) was added 1-acetyl-4-methoxy-5-methylindoline 29 (368 mg, 1.5 mmol) and the mixture was stirred at rt for 3 h. The red/brown solution was poured into ice-cold water and extracted with EtOAc. The combined organic phases were washed with saturated aq. NaHCO$_3$, brine, dried and evaporated to give a red viscous oil which after trituration with Et$_2$O-hexanes afforded 30 as red microcrystals (155 mg, 41%), mp 153–154° C. (from EtOAc-hexanes) (Found: C, 57.68; H, 5.62, N, 11.20. C$_{12}$H$_{14}$N$_2$O$_4$ requires C, 57.59; H, 5.64; N, 11.19%); λ$_{max}$ (EtOH)/nm 247 (ε/M⁻¹cm⁻¹ 22600), 329 (3120); λ$_{max}$ [EtOH-25 mM Na phosphate, pH 7.0 (2.5:97.5)]/nm 246 (ε/M⁻¹cm⁻¹ 18890), 338 (3260); ν$_{max}$ (Nujol)/cm⁻¹ 1670, 1600, 1515, 1375, 1335; δ$_H$ (90 MHz) 7.52 (1 H, s, 6-H), 4.22 (2 H, t, J 8.1, 2-H), 3.86 (3 H, s, OMe), 3.23 (3 H, t, 3-H), 2.25 (3 H, s, NAc) and 2.22 (3 H, s, Me).

2-(2-Dimethylamino-6-nitrophenyl) acetaldehyde semicarbazone 31. To a stirred solution of N,N-dimethyl-2-methyl-3-nitroaniline (5.40 g, 30 mmol) in dry DMF (30 ml) was added tris(dimethylamino)methane (6.54 g, 45 mmol) and the mixture was heated to 115° C. under N$_2$ for 4 h. The progress of the reaction was monitored by TLC [EtOAc-hexanes (1:3)]. The dark red solution was cooled in an ice bath, diluted with DMF (20 ml) and a solution of semicarbazide hydrochloride (3.51 g, 31.5 mmol) and conc. HCl (5.4 ml) in water (50 ml) was added. Stirring was continued for 30 min and the pH was raised to 5.0 and after stirring at 0° C. for 30 min, the pH was further raised to 7.5. The precipitated yellow solid was filtered, washed with ice-cold water and ether and dried under vacuum. Recrystallisation from aq. EtOH afforded 31 as yellow microcrystals (3.93 g, 49%), mp 156–157° C. (Found: C, 49.65; H, 5.70; N. 26.14. C$_{11}$H$_{15}$N$_5$O$_3$ requires C, 49.81; H, 5.70; N, 26.39%); ν$_{max}$ (Nujol)/cm⁻¹ 3450, 3160, 1720, 1600, 1525, 1350.

4-N,N-Dimethylaminoindole 32. A suspension of the semicarbazone 31 (6.37 g, 24 mmol) in EtOH (200 ml) was hydrogenated for 6 h at 60 psi over 10% Pd-C (1.35 g) and filtered. After evaporation of the filtrate, the residue was dissolved in EtOAc and washed with saturated aq. NaHCO$_3$ and brine, dried and evaporated to give a pink solid. Recrystallisation from EtOAc-hexanes and recovery of additional material by flash chromatography of the mother liquor [EtOAc-hexanes (1:3)] afforded 32 as white crystals (3.30 g, 86%), mp 104–106° C. (Found: C, 74.74; H. 7.61; N, 17.48. C$_{10}$H$_{12}$N$_2$ requires C, 74.97; H, 7.55; N, 17.48%); λ$_{max}$ (EtOH)/nm 222 (ε/M⁻¹cm⁻¹ 35860), 277 (10690); ν$_{max}$ (Nujol)/cm⁻¹ 3070, 1605, 1575, 1365; δ$_H$ (90 MHz) 8.12 (1 H, br s, NH), 6.84–7.24 (3 H, m, 2-, 6-, and 7-H), 6.46–6.70 (2 H, m, 3- and 5-H) and 2.99 (6 H, s, NMe$_2$).

1-Acetyl-4-N,N-dimethylaminoindoline 33. To a solution of 32 (0.80 g, 5 mmol) in dry THF (15 ml) cooled to 0° C. under N$_2$ was added slowly a 10 M solution of borane-methyl sulfide complex in THF (1.90 g, 2.37 ml, 25 mmol). The solution was then treated with TFA (10 ml, 130 mmol) and the mixture was stirred at 0° C. for 1 h, then at rt for a further 4 h. The progress of the reaction was followed by TLC [EtOAc-hexanes (4:1)] and after 5 h the solution was cooled to 0° C. and more BH$_3$.Me$_2$S (1 ml) was added. After a further 1 h at rt the solution was quenched with water (5 ml), basified to pH 11 with 2 M aq. NaOH and extracted with CH$_2$Cl$_2$. The combined organic phases were washed with brine, dried and evaporated. The residue was dissolved in a mixture of acetic anhydride (15 ml) and glacial acetic acid (15 ml) and stirred at rt overnight. The solution was concentrated in vacuo and the residue was dissolved in EtOAc and washed successively with 0.5 M aq. NaOH and brine, dried and evaporated to give a white solid. Flash chromatography [EtOAc-hexanes (4:1)] afforded 33 as white needles (0.77 g, 80%), mp 101–102° C. (from EtOAc-hexanes) (Found: C, 70.39; H, 7.91; N, 13.64. C$_{12}$H$_{16}$N$_2$O requires C, 70.56; H, 7.89; N, 13.71%); δ$_H$ (90 MHz) 7.87

(1 H, J 8.3, 7-H), 7.17 and 7.08 (1 H, dd, 6-H), 6.61 (1 H, d, 5-H) 4.03 (2 H, t, J 8, 2-H), 3.10 (2 H, t, 3-H), 2.76 (6 H, s, NMe$_2$) and 2.20 (3 H, s, NAc).

Nitration of 1-Acetyl-4-N,N-dimethylaminoindoline 33. To a stirred solution of NaNO$_3$ (204 mg, 2.4 mmol) in TFA (20 ml), cooled to −10° C., was added 1-acetyl-4-N,N-dimethylaminoindoline (408 mg, 2 mmol) and the mixture was stirred for 5 h, keeping the temperature below 0° C. The red/brown solution was poured into ice-cold water and extracted with EtOAc. The combined organic phases were washed with saturated aq. NaHCO$_3$ and brine, dried and evaporated to give a red viscous oil (640 mg). Flash chromatography [EtOAc-hexanes (9:1)] gave two fractions. The first product eluted was 1-acetyl-4-N,N-dimethylamino-5-nitroindoline 34 as fine orange needles (74 mg, 15%), mp 163–164° C. (from EtOAc-hexanes) (Found: C, 57.43; H, 6.01; N, 16.72. C$_{12}$H$_{15}$N$_3$O$_3$ requires C, 57.82; H, 6.07; N, 16.85%); $\lambda_{max}$ (EtOH)/nm 245 ($\epsilon$/M$^{-1}$cm$^{-1}$ 25310), 266 (24250), 332 (11550); $\lambda_{max}$ [EtOH-25 mM Na phosphate, pH 7.0 (2.5:97.5)]/nm 248 ($\epsilon$/M$^{-1}$cm$^{-1}$ 24840), 356 (11260); $v_{max}$ (Nujol)/cm$^{-1}$ 1665, 1595, 1385, 1305; $\delta_H$ (500 MHz) 7.93 (1 H, d, J 7.5, 7-H), 7.63 (1 H, d, J 8.5, 6-H), 4.14 (2 H, t, J 8.5, 2-H), 3.19 (2 H, t, 3-H), 2.80 (6 H, s, NMe$_2$) and 2.24 (3 H, s, N-Ac).

The second material eluted, a yellow solid (413 mg), was dissolved in a mixture of MeOH (75 ml), water (15 ml), and conc. HCl (7.5 ml) and heated under reflux for 3 h. The solution was diluted with water, concentrated in vacuo, basified to pH 12 and extracted with EtOAc. The combined organic phases were washed with brine, dried and evaporated to give a yellow solid (399 mg). Flash chromatography [EtOAc-hexanes (2:3)] gave two fractions. The first material eluted was processed as described below. The second product eluted was 4-N,N-dimethylamino-5,7-dinitroindoline 35 as bright red microcrystals (145 mg, 48%), mp 190–191° C. (from EtOAc-hexanes) (Found: C, 47.79; H, 4.81; N, 22.24. C$_{10}$H$_{12}$N$_4$O$_4$ requires C, 47.62; H, 4.80; N, 22.20%); $\lambda_{max}$ (EtOH)/nm 222 ($\epsilon$/M$^{-1}$cm$^{-1}$ 34080), 355 (45950); $\lambda_{max}$ [EtOH-25 mM Na phosphate, pH 7.0 (2.5:97.5)]/nm 225 ($\epsilon$/M$^{-1}$cm$^{-1}$ 31720), 374 (40630; $v_{max}$ (Nujol)/cm$^{-1}$ 3380, 1590, 1400, 1370, 1320, 1295; $\delta_H$ (90 MHz) 8.48 (1 H, s, 6-H), 6.96 (1H, br s, NH), 3.92 (2 H, t, J 9, 2-H), 3.20 (2 H, t, 3-H) and 2.91 (6 H, s, NMe$_2$).

The first eluted material from the above chromatography (48 mg) was dissolved in a mixture of acetyl chloride (5 ml) and acetic acid (5 ml) and heated under reflux for 6 h. The solution was poured into ice-water, basified to pH 12 with 2 M aq. NaOH and washed with CH$_2$Cl$_2$. The combined organic phases were washed with brine, dried and evaporated to give a brown viscous oil (66 mg). Flash chromatography [EtOAc-hexanes (9:1)] gave 1-acetyl-4-N,N-dimethylamino-7-nitroindoline 36 as yellow microcrystals (23 mg, 5%), mp 177–178° C. (from EtOAc-hexanes) (Found: C, 57.66; H, 6.04; N, 16.80. C$_{12}$H$_{15}$N$_3$O$_3$ requires C, 57.82; H, 6.07; N, 16.85%); $\lambda_{max}$ (EtOH)/nm 227 ($\epsilon$/M$^{-1}$cm$^{-1}$ 35220), 244 (34270) 280 (12610) 373 (16660); $\lambda_{max}$ [EtOH-25 mM Na phosphate, pH 7.0 (5:95)]/nm 235 ($\epsilon$/M$^{-1}$cm$^{-1}$ 30760), 401 (12020; $v_{max}$ (Nujol)/cm$^{-1}$ 1670, 1590, 1375; $\delta_H$ (500 MHz) 7.72 (1 H, d, J 9, 6-H), 6.52 (1 H, d, 5-H), 4.20 (2 H, t, J 8, 2-H), 3.15 (2 H, t, 3-H), 2.96 (6 H, s, NMe$_2$) and 2.22 3 H, s, N-Ac). The assignments were made from a combination of the 1-dimensional spectrum and nOe experiments.

Figure 4:
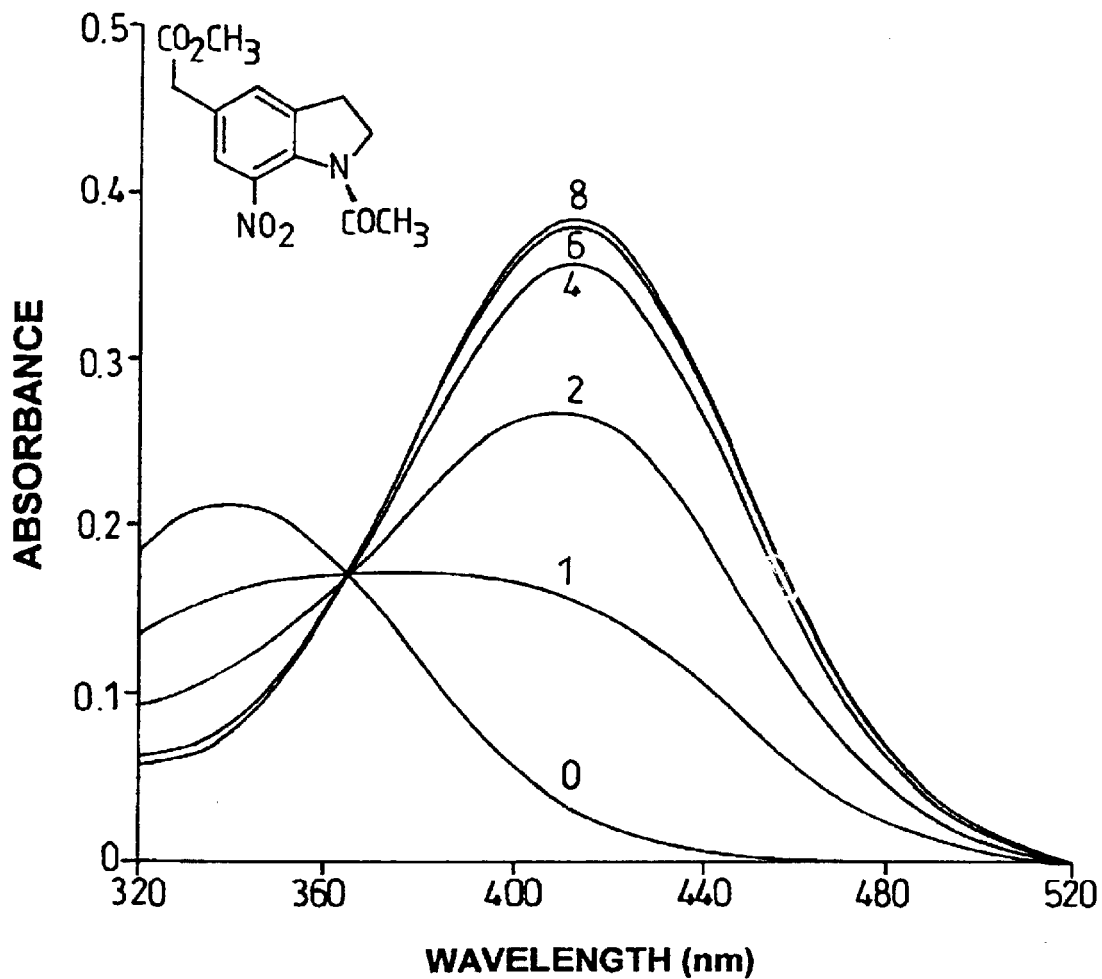
FIG. 4: Photolysis of 16 in pH 7 aqueous buffer. Numbers on the traces indicate the cumulative time of irradiation (in minutes).
Figure 5:
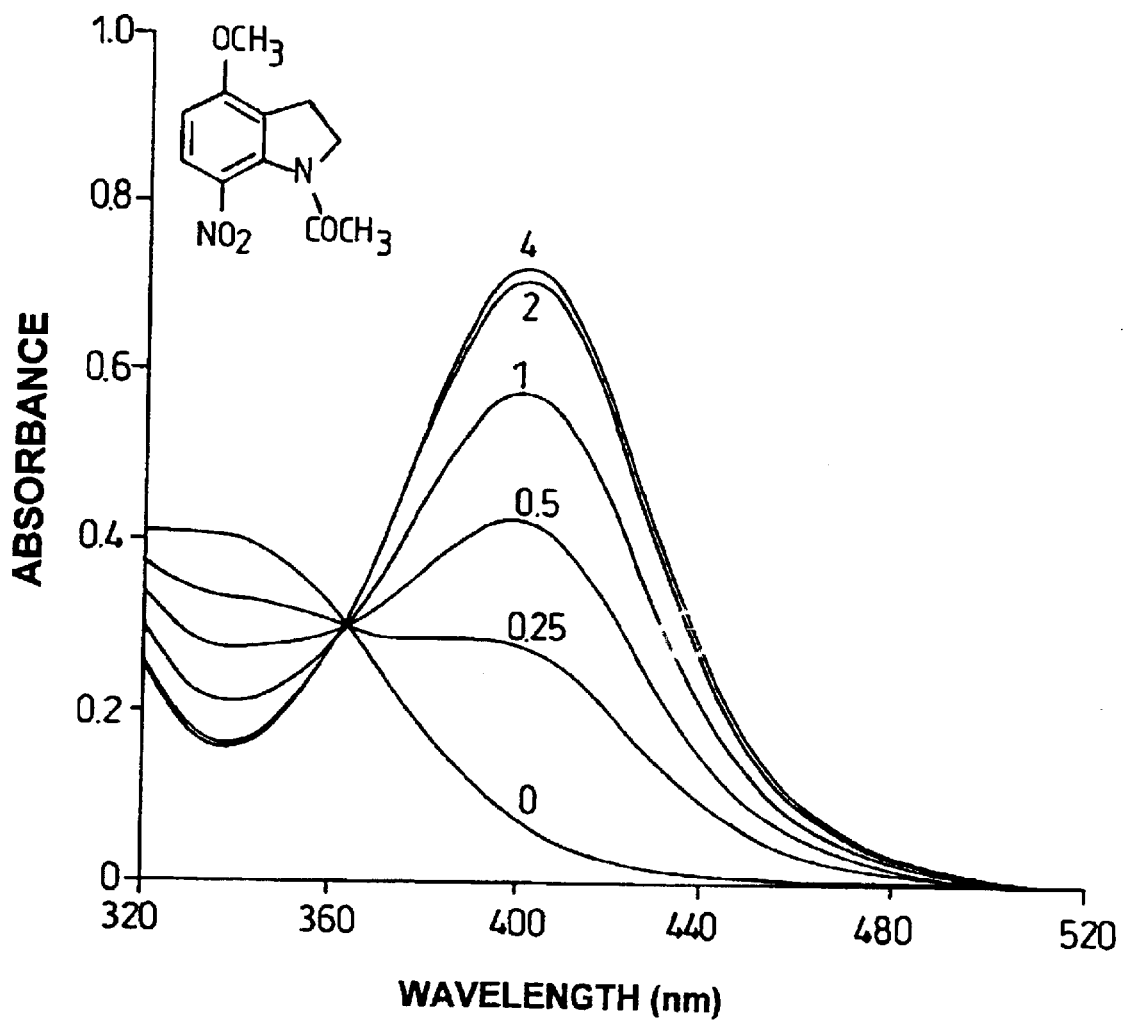
FIG. 5: Photolysis of 25 in pH 7 aqueous buffer. Numbers on the traces indicate the cumulative time of irradiation (in minutes).
Figure 6:
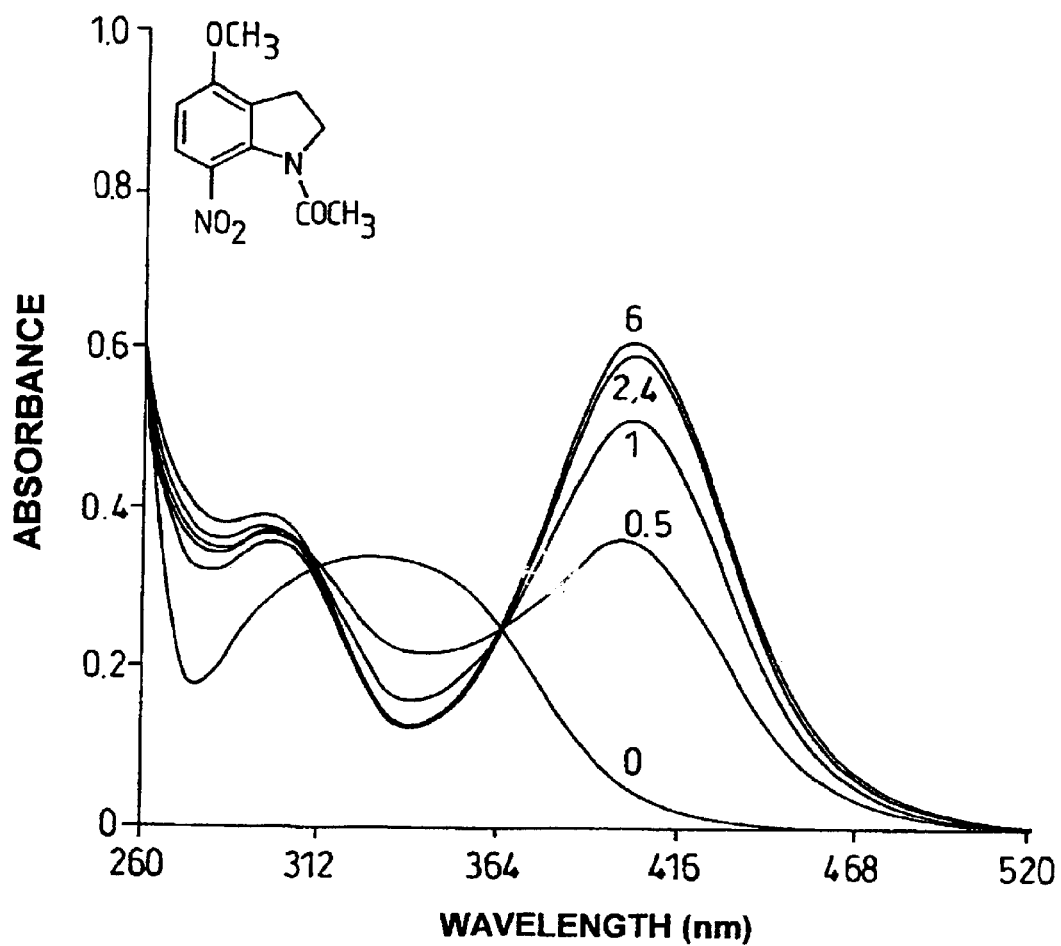
FIG. 6: Photolysis of 25 in pH 7 aqueous buffer. Numbers on the traces indicate the cumulative time of irradiation (in minutes).
Figure 7:
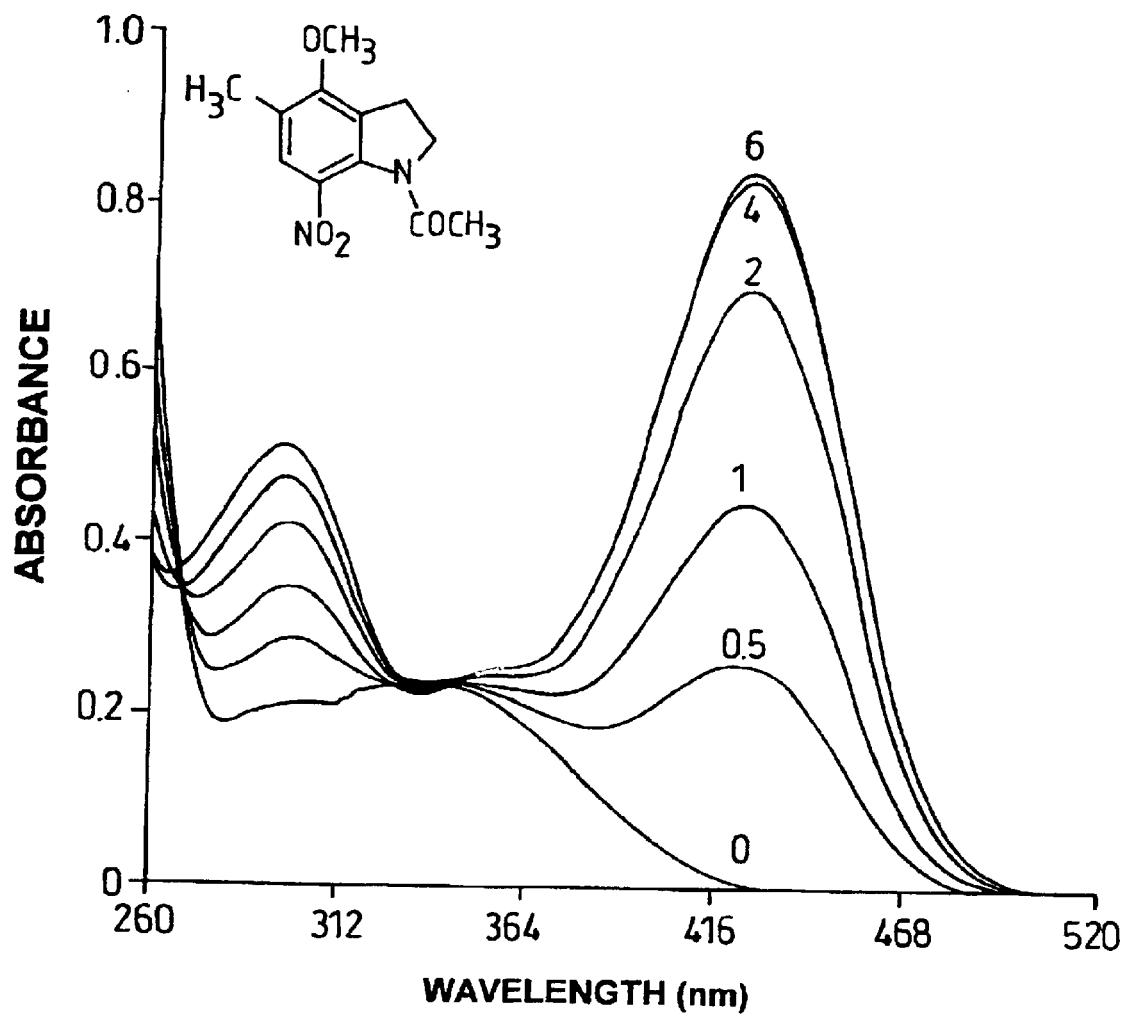
FIG. 7: Photolysis of 30 in pH 7 aqueous buffer. Numbers on the traces indicate the cumulative time of irradiation (in minutes).

Comparative photolysis of methyl 1-acetyl-7-nitroindoline-5-acetate 16 and 1-acetyl-4-methoxy-7-nitroindoline 25 in aqueous solution. Separate 1 ml samples of each compound [0.0896 mM in EtOH-25 mM Na phosphate, pH 7 (5:95)] in 1 cm path length optical cells were photolysed simultaneously for 0, 0.25, 0.5, 1, 2, 4, 6 and 8 min in a Rayonet photochemical reactor (16×350 nm lamps) and UV-VIS spectra were recorded after each irradiation period. FIGS. 4 and 5 show the time course of photolysis for 16 and 25 respectively. The times required for half-maximal photolysis were ~1.2 and 0.4 min respectively, indicating that photolysis of the methoxy compound 25 was ~3-fold more efficient than for Comparative photolysis of 1-acetyl-4-methoxy-7-nitroindoline 25 and 1-acetyl-4-methoxy-5-methylindoline 30 in aqueous solution. Separate 1 ml samples of each compound [0.0748 mM in EtOH-25 mM Na phosphate, pH 7 (5:95)] in 1 cm path length optical cells were photolysed simultaneously for 0, 0.25, 0.5, 1, 2, 4 and 6 min in a Rayonet photochemical reactor (16×350 nm lamps) and UV-VIS spectra were recorded after each irradiation period. FIGS. 6 and 7 show the time course of photolysis for 25 and 30 respectively. The times required for half-maximal photolysis were ~0.4 and 0.9 min respectively, indicating that photolysis of 25 was ~2-fold more efficient than for 30.

Discussion

The above experiments describe reagents based on 7-nitroindolines that undergo rapid and efficient photorelease of carboxylates, including L-glutamate, in aqueous solution at pH 7. As discussed in the background section, 5-bromo-7-nitroindoline reagents have previously been reported to undergo clean photosolvolysis in dioxane-CH$_2$Cl$_2$ that contained ~1% water to yield the carboxylic acid and the nitroindoline (6a). The detailed mechanism of that reaction was not investigated, although it was shown that the water present acted as a nucleophile, since [$^{18}$O] water gave $^{18}$O-labelled carboxylic acids and its replacement by alcohols or primary amines yielded esters or amides as photoproducts (6). As shown below, the reaction takes an entirely different course in aqueous solution.

The compounds 8–10 described here employed a blocking 5-substituent to direct nitration to the required 7-position. Previous work (6) used 5-bromo compounds but this heavy atom can result in less efficient photolysis by quenching the excited state and was therefore unsuitable in this context. Therefore, we used instead a —CH$_2$CO$_2$Me substituent as a blocking group, which was expected to confer better aqueous solubility and also provides a site for possible adjustment of solubility properties. The required indoline 3 was prepared by thallium(III) nitrate oxidation (7) of 1,5-diacetylindoline 1, followed by acidic methanolysis of 2 for selective removal of the 1-acetyl group. (Scheme 1). Acylation of 3 followed by nitration (TFA-NaNO$_3$) (8) concurrently removed tert-butyl protecting groups to give directly the water-soluble target compounds, that were readily purified by reverse-phase HPLC. This route avoids the difficult acylation of 7-nitroindolines (6b), especially with sensitive side chains such as in glutamic acid (9). Manipulations of functional groups in the N-acyl substituent subsequent to nitration was also possible, e.g. synthesis of the phosphate compound 9 as shown in Scheme 1. For comparison, the 5-bromo compound 11 was prepared by a related route, starting from 1-acetyl-5-bromoindoline (10).

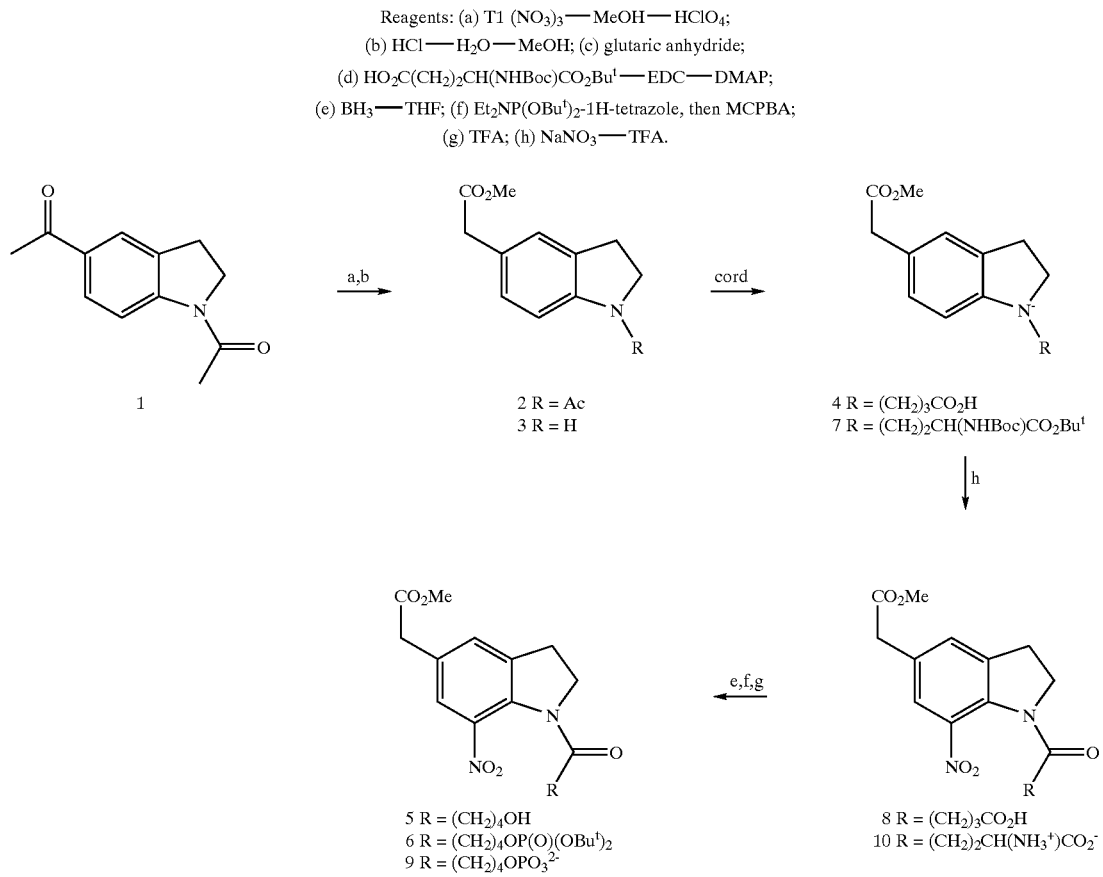

Scheme 1:

Reagents: (a) Tl(NO₃)₃—MeOH—HClO₄;
(b) HCl—H₂O—MeOH; (c) glutaric anhydride;
(d) HO₂C(CH₂)₂CH(NHBoc)CO₂Buᵗ—EDC—DMAP;
(e) BH₃—THF; (f) Et₂NP(OBuᵗ)₂-1H-tetrazole, then MCPBA;
(g) TFA; (h) NaNO₃—TFA.

Upon comparative photolysis of the 1-glutaryl derivatives 8 and 11 in aqueous solutions at pH 7 and without excluding atmospheric oxygen, the bromo compound 11 was indeed converted ~2.5-fold less efficiently than 8. Photolysis of 8 proceeded cleanly, as shown by an isosbestic point at 365 nm in spectra of a solution photolyzed for increasing times to at least 65% conversion, but the photoproduct of the protecting group was not the 7-nitroindoline 12 ($\lambda_{max}$ 450 nm) expected from the previous report (6a). Instead the product ($\lambda_{max}$ 412 nm) was shown to be the novel 7-nitrosoindole 13 (Scheme 2, R=CH₂CO₂Me) by NMR and mass spectroscopy. Further confirmation of the presence of a nitroso group was that treatment of 13, R=CH₂CO₂Me) with a thiol readily abolished the 412 nm chromophore, presumably by conversion to the corresponding hydroxylamine (11, 12). Quantitative amino acid analysis of part-photolyzed solutions of the glutamate derivative 10 showed that photolysis released glutamate from the starting compound in 1:1 stoichiometry (within experimental error), both in the absence and presence of dithiothreitol to react with the released nitrosoindole 13, R=CH₂CO₂Me). In control experiments, photolysis of the glutaryl compound 8 in CH₂Cl₂-dioxane-H₂O (2:3:0.05) cleanly gave the expected (6a) nitroindoline 12. Irradiation of equimolar solutions of 8 in aqueous solution or in the CH₂Cl₂-dioxane-H₂O mixture showed that photolysis in organic solvent was at least 2-fold more efficient than in water.

Formation of different products in different solvents requires a change of mechanism and there is some precedent for photoreactivity of nitroaryl compounds in aqueous solution that was not observed in organic solvents. This was suggested to arise from formation of a highly polarized π,π* triplet state in aqueous solution, in contrast to an π,π* state in organic solvents (13). First, flash photolysis of 9 (used because it was highly water-soluble and had no carboxylate group that might interfere with measurements on the carboxylate formed by photolysis) coupled with FTIR difference spectroscopy (12) showed the antisymmetric stretch of the released carboxylate at 1553 cm⁻¹ whether photolysis was performed in normal or [$^{18}$O]water (97 % isotopic abundance). Thus the oxygen atom introduced into the acyl group to form the carboxylate does not derive from the solvent. Second, we have investigated the kinetics of product formation, specifically of the released proton and carboxylate. Flash photolysis (320 nm laser, 1 ms pulse, 20° C.) coupled with time-resolved UV-VIS absorption spectroscopy (14) of a solution at pH 7 that contained 8 and a pH indicator (Bromothymol Blue) showed acidification of the solution upon irradiation. The major component of the signal (~85%) was complete within the laser pulse and the smaller component had a rate of ~9 s$^{-1}$. Time-resolved IR measurements (12) at 1557 cm$^{-1}$ following flash photolysis of 9 (351 nm laser, 9 ns pulse, spectral resolution 25 cm$^{-1}$, 25° C., pH 7) to monitor formation of the carboxylate showed an instantaneous decrease in absorption, arising from disappearance of the nearby nitro group absorption (1539 cm$^{-1}$), followed by biphasic absorption increase, with the major (~80%) and minor components having exponential rates of ~2700 and ~10 s$^{-1}$ respectively. The latter process may correspond with the slow phase of proton release described above. An overlapping band on the high-frequency side of the main 1553 cm$^{-1}$ band makes definitive interpretation of the signals uncertain. However, on the basis of the demonstrated release of carboxylates and initial biological testing (see below), we interpret the faster process as principally representing formation of the carboxylate ($t_{1/2}$ ~0.25 ms). A provisional mechanism to accommodate most of these data is shown in Scheme 2.

Scheme 2.

Suggested photolysis mechanism for 1-acyl-7-nitroindolines in aqueous solution.

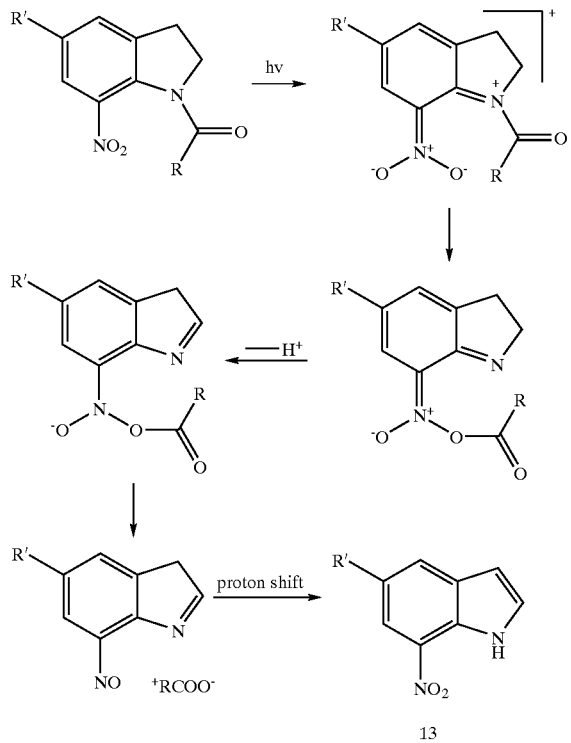

Oxygen transfer from the nitro to the acyl group has been previously demonstrated in photolysis of the related 1-acyl-8-nitrotetrahydroquinolines in a range of organic solvents, although the by-product from the heterocycle was not characterized (15). A feature of the sequence is that proton loss precedes release of the carboxylate, as is required by the observed reaction rates. However the mechanism does not account for the slower, minor processes observed for both the proton and carboxylate signals.

In addition to the release rate of the bioeffector species following flash irradiation, important properties of any caged compound include stability in aqueous solution and its extent of photolysis upon a single flash irradiation. The 1-acylnitroindolines were stable at pH 7; at pH 12, 30° C. the half-times for amide hydrolysis of 9 and 10 were 29 and 6 h respectively. The faster hydrolysis of the glutamate derivative 10 indicated that its free amino group competes with external base, presumably leading to formation of pyroglutamate.

In this context, hydrolytic stability refers to the amide bond. In all these compounds, the ester group in the side chain was slowly hydrolyzed at pH 7. However, in separate experiments, 10 and the salt of its corresponding free acid (isolated as a minor by-product during synthesis of 10) were found to release glutamate upon photolysis with equal efficiency. The ester hydrolysis is therefore unimportant. The stabilities quoted were from experiments on the free acids of the phosphate 9 and the glutamate derivative 10, and were determined from reverse-phase HPLC measurements of disappearance of starting compounds. The use of the free acids avoided analytical complications from the much faster cleavage of the ester group.

The results confirm that hydrolysis can be disregarded during purification, storage and use of these compounds at pH values near neutrality. The product quantum yield ($Q_p$) for photolysis of the glutamate derivative 10 was determined by laser flash irradiation (347 nm) of a solution containing 10 and 1-(2-nitrophenyl)ethyl phosphate (16) (both 0.5 mM in pH 7 phosphate buffer). Conversions by a single flash (~90 mJ) were 9.7 and 23% respectively (reverse-phase HPLC), leading to $Q_p$=0.043 by comparison with the known value (16) (0.54) for the caged phosphate and after correction for the different extinction coefficients at the irradiation wavelength. Although the value of $Q_p$ is low, the relatively high extinction coefficient at ~350 nm (~2700 M$^{-1}$cm$^{-1}$) compared to that of "classical" 2-nitrobenzyl-type caged compounds (~600 M$^{-1}$cm$^{-1}$) enables similar photolytic efficiency to be achieved.

The caged L-glutamate reagent 10 was tested in primary cultures of rat cerebellar granule neurones for its pharmacological actions and ability to effect photolytic activation of glutamate ion channels. All electrophysiological experiments were performed in Mg$^{2+}$-free mammalian Ringer's solution containing 100 μM glycine. Cells were voltage clamped at −65 mV with whole-cell patch clamp (17) and the glutamate sensitivity was established by responses to 20 ms pulses of L-glutamate, applied at a frequency of 0.25 Hz by iontophoresis from a 1-μm tipped glass pipette. In control experiments, replacing the bath solution with one containing 10 (1 mM) produced no activation of current in granule neurones and did not diminish the peak response to iontophoretic pulses of L-glutamate. Furthermore, using the phosphate 9 instead of the glutamate precursor 10, both with and without iontophoretic application of L-glutamate showed no effect of the caged compound before, during and after photolysis (see below). The control experiments during and after photolysis confirm that the by-product 13 has no adverse effect on glutamate receptors or resting membrane properties of granule neurones. Flash photolysis of caged glutamate 10, using a 1 ms pulse from a xenon arc flash lamp (20) through a Schott UG11 filter and focused to a 200 μm diameter spot at the preparation, resulted in a fast rise of inward current (FIG. 1) with exponential half-time of mean 0.74 ms (±0.13 ms S.D. n=8), followed by a decline comprising fast (mean half-time=2.9 ms) and slow time courses. The latter most likely arises from glutamate diffusion away from the photolyzed region. The time course of the initial decline may represent desensitization of non-NMDA glutamate channels.

During the slow decline there was a clear increase in the low frequency noise of the glutamate-activated current compared to baseline, consistent with gating of glutamate-activated ion channels. Thus, this data indicates that 10 is inactive at glutamate ion channels of both NMDA- and non-NMDA-activated types, and that the release of L-glutamate by flash photolysis of 10 is on the same time scale as the light pulse.

Thus, initial chemical and electrophysiological characterization indicates that 10 is a useful reagent for rapid photorelease of L-glutamate. The photochemistry is markedly solvent-dependent, with formation of the novel nitrosoindole 13 as the principal photolytic by-product in aqueous solution.

Substituent effects on the efficiency of photolysis have been examined using compounds bearing an acetyl group on the indoline nitrogen. It was aimed initially to study the 4-methoxy-substituted analogue of 16. Following an analogous route to that described in Scheme 1, 1-acetyl-4-methoxyindoline was treated with acetyl chloride under Friedel-Crafts conditions and the product ketone was oxidised with thalliuim(III) nitrate to give the corresponding methyl indolineacetate. Nitration (NaNO$_3$-TFA) gave a product that was initially assumed to be the required 3, but this material was photostable. It seemed that the first electrophilic substitution could have taken place at the 7-position rather than at C-5 as required. Single crystal X-ray diffraction analysis of the nitrated product confirmed this suspicion and the true sequence is therefore 1-acetyl-4-methoxyindoline-22–23–24.

Since Friedel-Crafts acylation of 1-acetyl-4-methoxyindoline occurred regiospecifically at the 7-position, its direct nitration was examined instead but in this case both the 7- and 5-nitro compounds 25 and 26 were obtained in equal proportion. Nevertheless, the two compounds were readily separated by chromatography and the regiochemistry was assigned for 25 by observation of a strong nOe enhancement between the methoxy group and an adjacent aromatic proton. The lack of regioselectivity in this reaction compared to the Friedel-Crafts acylation can be explained by higher reactivity of the electrophile in the nitration reaction. Comparative photolysis of aqueous solutions of 16 and 25 at equal concentration indicated that the latter photolysed with ~3-fold greater efficiency. The effect was sufficiently marked to warrant further exploration of substituent effects.

It was first considered whether a compound with a 5-substituent could be easily accessed, since that would overcome the lack of regioselectivity during nitration. For simplicity, a 5-methyl substituent was used. The required indole 27 was prepared from 2,6-dimethyl-3-nitroanisole by a Leimgruber-Batcho synthesis (26), reduced to the indoline 28 with NaBH$_3$CN-acetic acid (27) and acetylated to give 29. Nitration with NaNO$_3$-TFA then gave 30 as a single isomer. Photolysis of 30 in aqueous solution was ~2-fold less efficient than for 25, which lacks a 5-substituent, perhaps because the 5-methyl group causes steric inhibition of optimal orbital overlap of the methoxy group with the aromatic ring.

With the relative merits of the substitution pattern on the aromatic ring established, the effect of the more powerfully electron-releasing 4-dimethylamino group was probed. The required indole 32 was prepared via the semicarbazone 31 from N,N-dimethyl-2-methyl-3-nitroaniline by a modified Leimgruber-Batcho procedure (30). Reduction to the corresponding indoline was achieved in good yield with BH$_3$.Me$_2$S-TFA (31) and the product was acetylated to give 1-acetyl-4-N,N-dimethylaminoindoline 33. Nitration as before with NaNO$_3$-TFA gave a complex mixture, from which the 5-nitro compound 34 was separated by chromatography. To achieve isolation of the required 7-nitro isomer 36, the remaining material was hydrolysed and the products chromatographed. The 5,7-dinitroindoline 35 was obtained in pure form, together with fractions that contained the presumed 7-nitroindoline. Acetylation of these combined fractions provided the desired material 36 in poor overall yield. Its structure was confirmed by nOe enhancement of the 5-proton upon irradiation of the dimethylamino signal. In the related 5-nitro isomer 34, irradiation of the dimethylamino signal had no effect on the integrated intensity of either aromatic proton signal. Upon irradiation of 36 in aqueous solution with near-UV light, as for the compounds 16, 25 and 30, there was no detectable photolysis as assessed by the lack of any change in the UV-visible spectrum of the irradiated solution. The series of compounds described in this latter series of experiments could be coupled to effector moieties, e.g. as described for compounds 10 and 21.

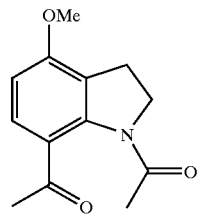

22

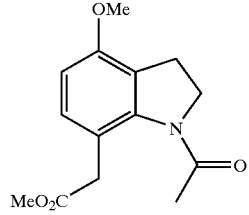

23

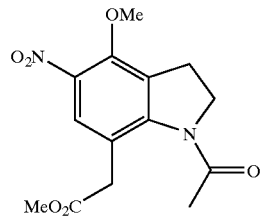

24

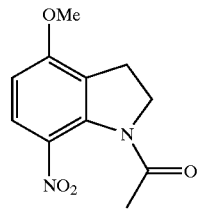

25

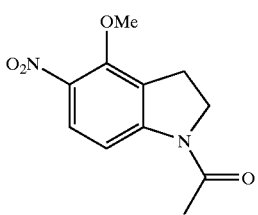
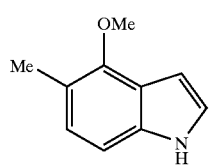
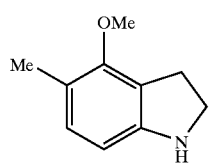
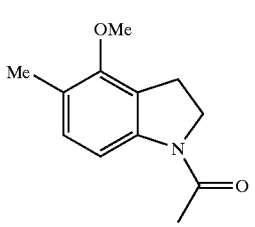
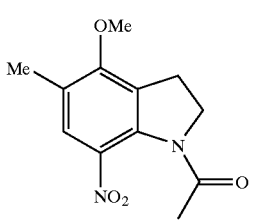
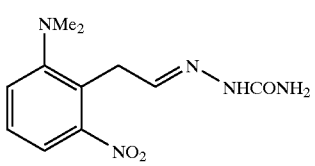
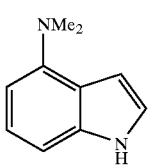
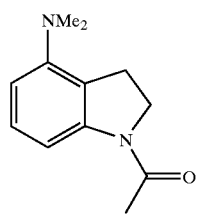

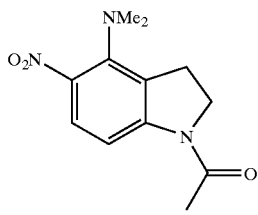
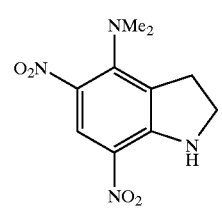
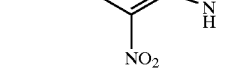
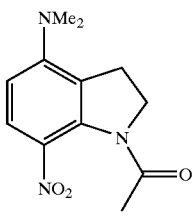

REFERENCES

The reference mentioned herein are all incorporated by reference in their entirety.

1a. Adams & Tsien, *Annu. Rev. Physiol.* 1993, 55, 755.
1b. Corrie & Trentham. In *Bioorganic Photochemistry;* Morrison, H., Ed.; Wiley, New York, 1993; Vol. 2, pp 243–305.
1c. Kaplan, *Annu. Rev. Physiol.* 1990, 52, 897.
2. See references (3) to (7) of Papageorgiou & Corrie, *Tetrahedron* 1999, 55, 237.
3. Givens et al, *J. Am. Chem. Soc.* 1997, 119, 8369.
4. Furuta et al, *Proc. Natl. Acad. Sci. USA* 1999, 96, 1193.
5. Papageorgiou & Corrie, *Tetrahedron* 1997, 53, 3917.
6a. Amit et al, *J. Am. Chem. Soc.* 1976, 98, 843.
6b. Pass et al, *J. Am. Chem. Soc.* 1991, 103, 7674.
7. McKillop et al, *J. Am. Chem. Soc.* 1971, 93, 4920.
8. Mortensen et al, *Org. Prep. Proced. Int.* 1996, 28, 123.
9. Carpino et all: *Acc. Chem. Res.,* 1996, 29, 268.
10. Gall et al, *J. Org. Chem.* 1955, 20, 1538.
11. Zuman & Shah, *Chem. Rev.* 1994; 94, 1621.
12. Barth et al, *J. Am. Chem. Soc.* 1997, 119, 4149.
13a. Wan & Yates, *Can. J. Chem.* 1986, 64, 2076.
13b. Wan & Muralidharan, *J. Am. Chem. Soc.* 1988, 110, 4336.
14. Walker et al, *J. Am. Chem. Soc.* 1988, 110, 7170.
15. Amit et al, *J. Chem. Soc.,* Perkin Trans. 1 1976, 57.
16. Kaplan et al, *Biochemistry* 1978, 17, 1929.
17. Hamill et al, *Pflügers Archiv* 1981, 391, 85.
18. Rapp & Güth, *Pflügers Archiv* 1985, 411, 200.
19. Khodakhah & Ogden, *J. Physiol.* 1995, 487, 343.
20. Crabb & Soilleux, *J. Chem. Soc., Perkin Trans.* 1 1985, 1381.
21. Gall et al, *J. Org. Chem.* 1955, 20, 1538.
22. Morno & Sewell, *J. Chem. Soc.* (B), 1971, 1227.
23. Terentev et al, *J. Gen. Chem. USSR* 1959, 29, 2835.
24. Kaplan etal, *Biochemistry* 1978, 17, 1929.
25. Corrie et al, *J. Chem. Soc. Perkin Trans.,* 1, 1992, 1015–1019.

26. Kawase, Sinhababu & Borchardt. *J. Heterocycl. Chem.* 1987, 24, 1499; Buchanan, Stoddart & Wightman. *J. Chem. Soc., Perkin Trans.* 1 1994, 1417.
27. Gangjee, Vasudevan & Queener. *J. Med. Chem.* 1997, 40, 479.
28. Wieland & Unger. *Chem. Ber.* 1963, 96, 253.
29. Esser, Stahle, Sullke, Muramatsu, Kitagawa & Uhida, German Patent DE19514579.
30. Kruse, *Heterocycles* 1981, 16, 1119.
31. Maryanoff & McComsey, U.S. Pat. No. 4,210,590.
32. Adams et al, *J. Am. Chem. Soc.,* 1989, 111, 7957–7968.

What is claimed is:

1. A compound represented by the structural formula:

wherein
 $R_1$ is hydrogen;
  $C_{1-10}$ alkyl or substituted alkyl;
  ;$O(CH_2)_n$—Y
  $N(COZ)(CH_2)_mY$; or
  $N[(CH_2)_mQ][(CH_2)_ny]$;
 $R_2$ and $R_3$ are independently selected from:
  hydrogen;
  $C_{1-10}$ alkyl or substituted alkyl; or
  $R_2$ and $R_3$ together are cycloalkyl;
 $R_4$ is hydrogen;
  $C_{1-10}$ alkyl or substituted alkyl;
  phenyl or substituted phenyl;
  $(CH_2)_nY$; or
  $(CH_2)_mO(CH_2)_nY$;
 wherein:
  m and n are independently between 1 and 10;
  Q and Y are independently selected from hydrogen, $CO_2H$ or salts thereof or $OPO_3^{2-}$;
  Z is hydrogen or $C_{1-10}$ alkyl or substituted alkyl; and,
 X represents an amino acid.

2. A compound represented by the structural formula:

wherein
 $R_2$ and $R_3$ are independently selected from hydrogen, $C_{1-10}$ alkyl or substituted alkyl, or $R_2$ and $R_3$ together are cycloaklyl;
 $R_4'$ is a blocking group; and,
 X represents an amino acid.

3. The compound of claim 2, wherein $R_4'$ is selected from:
 hydrogen;
 $C_{1-10}$ alkyl or substituted alkyl;
 phenyl or substituted phenyl;
 $(CH_2)_nCO_2Y$; and,
 $(CH_2)_n$—O—$(CH_2)_mY$;
wherein:
 m and n are independently between 0 and 10; and,
 Y is hydrogen, or $C_{1-10}$ alkyl or substituted alkyl.

4. The compound of claim 1, or a salt thereof, wherein the compound is:
 Methyl 1-[S-(4-amino-4-carboxybutanoyl)]-7-nitroindoline-5-acetate 10;
 Methyl 1-(4-aminobutanoyl)-7-nitroindoline-5-acetate 21;
 1-[S-(4-Amino-4-carboxybutanoyl)]-4-methoxy-7-nitroindoline;
 1-(4-Aminobutanoyl)-4-methoxy-7-nitroindoline;
 1-[S-(4-Amino-4-carboxybutanoyl)]-4-methoxy-5-methyl-7-nitroindoline; or
 1-(4-Aminobutanoyl)-4-methoxy-5-methyl-7-nitroindoline.

5. The compound of claim 2, or a salt thereof, wherein the compound is:
 Methyl 1-[S-(4-amino-4-carboxybutanoyl)]-7-nitroindoline-5-acetate 10;
 Methyl 1-(4-aminobutanoyl)-7-nitroindoline-5-acetate 21;
 1-[S-(4-Amino-4-carboxybutanoyl)]-4-methoxy-7-nitroindoline;
 1-(4-Aminobutanoyl)-4-methoxy-7-nitroindoline;
 1-[S-(4-Amino-4-carboxybutanoyl)]-4-methoxy-5-methyl-7-nitroindoline; or
 1-(4-Aminobutanoyl)-4-methoxy-5-methyl-7-nitroindoline.

6. The compound of claim 1, wherein X represents a neuroactive amino acid selected from the group of L-glutamate, GABA or glycine.

7. The compound of claim 2, wherein X represents a neuroactive amino acid selected from the group of L-glutamate, GABA or glycine.

8. A composition comprising a compound of claim 1 and a pharmaceutically acceptable excipient or carrier.

9. A composition comprising a compound of claim 2 and a pharmaceutically acceptable excipient or carrier.

10. A composition comprising a compound of claim 3 and a pharmaceutically acceptable excipient or carrier.

11. A composition comprising a compound of claim 4 and a pharmaceutically acceptable excipient or carrier.

12. A composition comprising a compound of claim 5 and a pharmaceutically acceptable excipient or carrier.

13. The compound of claim 1, wherein said amino acid is a neuroactive amino acid.

14. The compound of claim 2, wherein said amino acid is a neuroactive amino acid.

15. The compound of claim 3, wherein said amino acid is a neuroactive amino acid.

16. A composition comprising a compound of claim 13 and a pharmaceutically acceptable excipient or carrier.

17. A composition comprising a compound of claim 14 and a pharmaceutically acceptable excipient or carrier.

18. A composition comprising a compound of claim 15 and a pharmaceutically acceptable excipient or carrier.

* * * * *